US009795661B2

(12) United States Patent
Casares et al.

(10) Patent No.: US 9,795,661 B2
(45) Date of Patent: Oct. 24, 2017

(54) TH1/TH2 POLARIZING VACCINES

(75) Inventors: Sofia A. Casares, Potomac, MD (US); Thomas L. Richie, Glenelg, MD (US); Teodor D. Brumeanu, Potomac, MD (US)

(73) Assignee: The United States of America as represented by the Secretary of the Navy, Arlington, VA (US)

(*) Notice: Subject to any disclaimer, the term of this patent is extended or adjusted under 35 U.S.C. 154(b) by 0 days.

(21) Appl. No.: 12/914,555

(22) Filed: Oct. 28, 2010

(65) Prior Publication Data

US 2012/0195893 A1 Aug. 2, 2012

Related U.S. Application Data

(60) Provisional application No. 61/284,357, filed on Nov. 16, 2009.

(51) Int. Cl.

| | |
|---|---|
| ***A61K 39/015*** | (2006.01) |
| ***C07K 14/55*** | (2006.01) |
| ***C07K 16/28*** | (2006.01) |
| ***C07K 14/54*** | (2006.01) |
| ***C07K 14/705*** | (2006.01) |
| *A61K 39/00* | (2006.01) |

(52) U.S. Cl.

CPC ........ *A61K 39/015* (2013.01); *C07K 14/5412* (2013.01); *C07K 14/5434* (2013.01); *C07K 14/55* (2013.01); *C07K 14/70532* (2013.01); *C07K 16/2851* (2013.01); *A61K 2039/57* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 2002/0044948 | A1 | 4/2002 | Khleir | |
| 2002/0098184 | A1 | 7/2002 | Heath | |
| 2002/0187131 | A1* | 12/2002 | Hawiger et al. | 424/93.7 |
| 2003/0171551 | A1* | 9/2003 | Rosenblatt et al. | 530/388.8 |
| 2004/0234531 | A1 | 11/2004 | Casares | |
| 2007/0178065 | A1 | 8/2007 | Lattime | |
| 2008/0199495 | A1 | 8/2008 | Boyd | |
| 2008/0254134 | A1 | 10/2008 | Brayden | |
| 2009/0053265 | A1 | 2/2009 | Corradin | |

FOREIGN PATENT DOCUMENTS

| | | | |
|---|---|---|---|
| WO | 2004076489 A1 | 9/2004 | |
| WO | WO 2007/098718 A1 | 9/2007 | |

OTHER PUBLICATIONS

Ruiz-Perez et al., Expression of the Plasmodium falciparum Immunodominant Epitope (NANP)4 on the Surface of *Salmonella enterica* Using the Autotransporter MisL, 2002, Infection and Immunity, vol. 70, No. 7, pp. 3611-3620.*

MacNamara et al., T-Cell Epitope Prediction: Rescaling Can Mask Biological Variation between MHC Molecules, 2009, PLoS Computational Biology, vol. 5, No. 3, pp. 1-7.*

Freeman, Gordon J., Bousslotis, Vassiiiki, Anumanthan, Anukanth, Bernstein, Gregory M., Ke, Xiao-Yen, Rennert, Paul D., Gray, Gary S., Gribben, John G., and Nadler, Lee M.; B7-1 and B7-2 Do Not Deliver Identical Costimulatory Signals, Since B7-2 but Not B7-1 Preferentially Costimulates the Initial Production of IL-4; Immunity, vol. 2, 523-532, May 1995, Copyright 1995 by Cell Press.

Rutitzky, Laura I., Hernandez, Hector J., and Stadecker, Miguel J.; Th1-polarizing immunization with egg antigens correlates with severe exacerbation of immunopathology and death in schistosome infection; PNAS, Nov. 6, 2001, vol. 98, No. 23, 13243-13248; www.pnas.org/cgi/doi/10.1073/pnas.231258498.

Butler, Matt, Morel, Anne-Sophie, Jordan, William J., Eren Efrem, Hue, Susan, Shrimpton, Rachel E. and Ritter, Mary A.; Altered expression and endocytic function of CD205 in human dendritic cells, and detection of a CD205-DCL-1 fusion protein upon dendritic cell maturation; 2006 Blackwell Publishing Ltd, Immunology, 120, 362-371.

Mukhopadhaya, A. et al. Selective Delivery of b cell antigen to dendritic cells in vivo leads to deletion and tolerence of autoreactive CD8+ T cells in NOD mice, PNAS vol. 105:17 p. 6374-6379 (2008).

Trumpfheller C. et al. The Microbial mimic poly IC induces durable and protective CD+ T cell immunity together with a dendritic cell targeted vaccine. PNAS vol. 105:7 p. 2574-2579 (2008).

Demangel C. et al. Single chain antibody fragments for the selective targeting of antigens to dendritic cells. Molecular Immunology. 42(2005) 979-985.

Lunde E et al: "Efficient delivery of T cell epitopes to APC by use of MHC class II-specific troybodies", The Journal of Immunology, The American Association of Immunologists, US, vol. 168, Jan. 1, 2002 (Jan. 1, 2002), pp. 2154-2162, XP002983188, ISSN: 0022-1767 *the whole document*.

Lunde E et al: "Troybodies and pepbodies", Biochemical Society Transactions, Portland Press Ltd, GB, vol. 30, No. Part 4, Jan. 1, 2002 (Jan. 1, 2002), pp. 500-506, XP002227237, ISSN: 0300-5127, DOI: 10.1042/BST0300500 *the whole document*.

Tunheim Gro et al: "Human CD14 is an efficient target for recombinant immunoglobulin vaccine constructs that deliver T cell epitopes", Journal of Leukocyte Biology, Federation of Americansocieties for Experimental Biology, US, vol. 77, No. 3, Mar. 1, 2005 (Mar. 1, 2005), pp. 303-310, XP002432577, ISSN: 0741-5400, DOI: 10.1189/JLB.0804480 *the whole document*.

Brumeanu T-D et al: Presentation of a viral peptide assembled on the carbohydrate moieties of immunoglobulin does not require processing, European Journal of Immunology, Wiley- V C H Verlag GMBH & Co. KGAA, DE, vol. 27, No. 9, Jan. 1, 1997 (Jan. 1, 1997), pp. 2408-2416, XP002088231, ISSN: 0014-2980, DOI: 10.1002/EJI.1830270940 *the whole document*.

(Continued)

*Primary Examiner* — Benjamin P Blumel

(74) *Attorney, Agent, or Firm* — Ning Yang; Albert M. Churilla; Diane P. Tso

(57) ABSTRACT

The present invention relates to recombinant chimeric molecules that are capable of providing T cell receptor (TCR) interaction and costimulation for activation and differentiation of pathogen-specific T cells toward effector T helper 1 (Th1) or T helper 2 (Th2) cells. The chimera may capable of elicit antibodies against pathogen-specific B cell epitope(s). The present invention also relates method of using these chimeric molecules in whole or as a component of a vaccine.

19 Claims, 20 Drawing Sheets

(56) References Cited

OTHER PUBLICATIONS

Lunde E et al: "'Troy bodies': antibodies as vector proteins for T cell epitopes", Biomolecular Engineering, Elsevier, New York, NY, US, vol. 18, No. 3, Oct. 15, 2001 (Oct. 15, 2001), pp. 109-116, XP004305908, ISSN: 1389-0344, DOI: 10.1016/S1389-0344(01)00091-0 *the whole document*.

Tunheim et al: "Recombinant antibodies for delivery of antigen: a single loop between—strands in the constant region can accommodate long, complex and tandem T cell epitopes", International Immunology, vol. 20, No. 3, Jan. 1, 2008 (Jan. 1, 2008), pp. 295-306, XP055058657, ISSN: 0953-8178, DOI: 10.1093/intimm/dxm141 *the whole document*.

Hawiger D et al: "Dendritic cells induce peripheral T cell unresponsiveness under steady state conditions in vivo", The Journal of Experimental Medicine, Rockefeller University Press, US, vol. 194, No. 6, Sep. 17, 2001 (Sep. 17, 2001), pp. 769-779, XP002376445, ISSN:0022-1007, DOI: 10.1084/JEM.194.6.769 *the whole document*.

Casares S et al: "Foreign Peptides Expressed in Engineered Chimeric Self Molecules", Biotechnology and Genetic Engineering Reviews, Intercept Ltd., Andover, GB, vol. 15, Jan. 1, 1998 (Jan. 1, 1998), pp. 159-198, XP009069478, ISSN: 0264-8725 *the whole document*.

Hudson P J et al: "Engineered antibodies", Nature Medicine, Nature Publishing Group, New York, NY, US, vol. 9, No. 1, Jan. 1, 2003 (Jan. 1, 2003), pp. 129-134, XP002338941, ISSN: 1078-8956, DOI: 10.1038/NM0103-129 *the whole document*.

* cited by examiner

SEQUENCE LISTING

<160> NUMBER OF SEQ ID NOS: 19

<210> SEQ ID NO 1
<211> LENGTH: 2334
<212> TYPE: DNA
<213> ORGANISM: Artificial Sequence
<220> FEATURE:
<223> OTHER INFORMATION: Nucleotide sequence of PyBTh1 heavy chain

<400> SEQUENCE: 1
gcactgaagc ttgtcctgat tgcctcagcc ttcagttttc aaatccagtc agtggtcatc 60
cctgaaaaca gacctttcac catgaagttg tggctgaact ggattttcct tctaacactt 120
ttaaaagata tccagtgtga ggtgaagctg ttggaatctg gaggaggttt ggtacagccg 180

-continued

```
gggggttctc tgagactctc ctgtgcagct tctggattca ccttcaatga tttctacatg    240
aactggatcc gccagcctcc agggcaggca cctgagtggt tgggtgttat tagaaacaaa    300
ggtaatggtt acacaacaga ggtcaataca tctgtgaagg ggcggttcac catctccaga    360
gataataccc aaaacatcct ctatcttcaa atgaacagcc tgagagctga ggacaccgcc    420
atttactact gtgcaagagg cggtccttat tactacagtg gtgacgacgc cccttactgg    480
ggccaaggag tcatggtcac agtctcctca gccaaaacaa cagccccatc ggtataccca    540
ctggcccctg tgtgtggaga tacaactggc tcctcggtga ctctaggatg cctggtcaag    600
ggttatttcc ctgagccagt gaccttgacc tggaactctg gatccctgtc cagtggtgtg    660
cacaccttcc cagctgtcct gcagtctgac ctctacaccc tcagcagctc agtgactgta    720
acctcgagca cctggcccag ccagtccatc acctgcaatg tggcccaccc ggcaagcagc    780
accaaggtgg acaagaaaat tgagcccaga gggcccacaa tcaagccctg tcctccatgc    840
aaatgcccag cacctaacct cttgggtgga ccatccgtct tcatcttccc tccaaagatc    900
aaggatgtac tcatgatctc cctgagcccc atagtcacat gtgtggtggt ggatgtgagc    960
gaggatgacc cagatgtcca gatcagctgg tttgtgaaca acgtggaagt acacacagct   1020
cagacacaaa cccatagaga ggattacaac agtactctcc gggtggtcag tgccctcccc   1080
atccagcacc aggactggat gagtggcaag gagttcaaat gcaaggtcaa caacaaagac   1140
ctcccagcgc ccatcgagag aaccatctca aaacccaaag ggtcagtaag agctccacag   1200
gtatatgtct tgcctccacc agaagaagag atgactaaga aacaggtcac tctgacctgc   1260
atggtcacag acttcatgcc tgaagacatt tacgtggagt ggaccaacaa cgggaaaaca   1320
gagctaaact acaagaacac tgaaccagtc ctggactctg atggttctta cttcatgtac   1380
agcaagctga gagtggaaaa gaagaactgg gtggaaagaa atagctactc ctgttcagtg   1440
gtccacgagg gtctgcacaa tcaccacacg actaagagct tctcccaaac tccgggtaaa   1500
ggaggtggtg gagggggagg cggtcaaggc ccaggggcac cacaggggcc tggtgcccca   1560
caaggaccgg gtgctcctca gggacccggg gcgccccaac agccgccaca gcaaccccca   1620
caacagcctc cgcaacaacc accgcagcag ccccctggag gtggtggatc cggtggaggg   1680
ggaagtggag gtggagggtc tgttgatgaa caactgtcca agtcagtgaa agataaggta   1740
ttgctgcctt gccgttacaa ctctcctcat gaagatgagt gtgaagaccg aatctactgg   1800
caaaaacatg acaaagtggt gctgtctgtc attgctggga aactaaaagt gtggcccgag   1860
tataagaacc ggactttata tgacaacact acctactctc ttatcatcct gggcctggtc   1920
ctttcagacc ggggcacata cagctgtgtc gttcaaaaga aggaaagagg aacgtatgaa   1980
gttaaacact tggctttagt aaagttgtcc atcaaagctg acttctctac ccccaacata   2040
actgagtctg gaaacccatc tgcagacact aaaaggatta cctgctttgc ttccgggggt   2100
ttcccaaagc ctcgcttctc ttggttggaa aatggaagag aattacctgg catcaatacg   2160
acaatttccc aggatcctga atctgaattg tacaccatta gtagccaact agatttcaat   2220
acgactcgca accacaccat taagtgtctc attaaatatg gagatgctca cgtgtcagag   2280
gacttcacct gggaaaaacc cccagaagac cctcctgata gcaagtgatc taga         2334
```

<210> SEQ ID NO 2
<211> LENGTH: 2178
<212> TYPE: DNA
<213> ORGANISM: Artificial Sequence
<220> FEATURE:
<223> OTHER INFORMATION: Nucleotide sequence of PyTh1 heavy chain

<400> SEQUENCE: 2

```
gcactgaagc ttgtcctgat tgcctcagcc ttcagttttc aaatccagtc agtggtcatc      60
cctgaaaaca gacctttcac catgaagttg tggctgaact ggattttcct tctaacactt     120
ttaaaagata tccagtgtga ggtgaagctg ttggaatctg gaggaggttt ggtacagccg     180
gggggttctc tgagactctc ctgtgcagct tctggattca ccttcaatga tttctacatg     240
aactggatcc gccagcctcc agggcaggca cctgagtggt tgggtgttat tagaaacaaa     300
ggtaatggtt acacaacaga ggtcaataca tctgtgaagg ggcggttcac catctccaga     360
gataataccc aaaacatcct ctatcttcaa atgaacagcc tgagagctga ggacaccgcc     420
atttactact gtgcaagagg cggtccttat tactacagtg gtgacgacgc cccttactgg     480
ggccaaggag tcatggtcac agtctcctca gccaaaacaa cagccccatc ggtataccca     540
ctggcccctg tgtgtggaga tacaactggc tcctcggtga ctctaggatg cctggtcaag     600
ggttatttcc ctgagccagt gaccttgacc tggaactctg gatccctgtc cagtggtgtg     660
cacaccttcc cagctgtcct gcagtctgac ctctacaccc tcagcagctc agtgactgta     720
acctcgagca cctggcccag ccagtccatc acctgcaatg tggcccaccc ggcaagcagc     780
accaaggtgg acaagaaaat tgagcccaga gggcccacaa tcaagccctg tcctccatgc     840
aaatgcccag cacctaacct cttgggtgga ccatccgtct tcatcttccc tccaaagatc     900
aaggatgtac tcatgatctc cctgagcccc atagtcacat gtgtggtggt ggatgtgagc     960
gaggatgacc cagatgtcca gatcagctgg tttgtgaaca acgtggaagt acacacagct    1020
cagacacaaa cccatagaga ggattacaac agtactctcc gggtggtcag tgccctcccc    1080
atccagcacc aggactggat gagtggcaag gagttcaaat gcaaggtcaa caacaaagac    1140
ctcccagcgc ccatcgagag aaccatctca aaacccaaag ggtcagtaag agctccacag    1200
gtatatgtct tgcctccacc agaagaagag atgactaaga aacaggtcac tctgacctgc    1260
atggtcacag acttcatgcc tgaagacatt tacgtggagt ggaccaacaa cgggaaaaca    1320
gagctaaact acaagaacac tgaaccagtc ctggactctg atggttctta cttcatgtac    1380
agcaagctga gagtggaaaa gaagaactgg gtggaaagaa atagctactc ctgttcagtg    1440
gtccacgagg gtctgcacaa tcaccacacg actaagagct tctcccaaac tccgggtaaa    1500
ggaggtggtg gatccggtgg agggggaagt ggaggtggag ggtctgttga tgaacaactg    1560
tccaagtcag tgaaagataa ggtattgctg ccttgccgtt acaactctcc tcatgaagat    1620
gagtgtgaag accgaatcta ctggcaaaaa catgacaaag tggtgctgtc tgtcattgct    1680
gggaaactaa aagtgtggcc cgagtataag aaccggactt tatatgacaa cactacctac    1740
tctcttatca tcctgggcct ggtcctttca gaccggggca catacagctg tgtcgttcaa    1800
aagaaggaaa gaggaacgta tgaagttaaa cacttggctt tagtaaagtt gtccatcaaa    1860
gctgacttct ctacccccaa cataactgag tctggaaacc catctgcaga cactaaaagg    1920
attacctgct ttgcttccgg gggtttccca aagcctcgct tctcttggtt ggaaaatgga    1980
agagaattac ctggcatcaa tacgacaatt tcccaggatc ctgaatctga attgtacacc    2040
attagtagcc aactagattt caatacgact cgcaaccaca ccattaagtg tctcattaaa    2100
tatggagatg ctcacgtgtc agaggacttc acctgggaaa aacccccaga agaccctcct    2160
gatagcaagt gatctaga                                                 2178
```

<210> SEQ ID NO 3

```
<211> LENGTH: 2070
<212> TYPE: DNA
<213> ORGANISM: Artificial Sequence
<220> FEATURE:
<223> OTHER INFORMATION: Nucleotide sequence of PyBTh2 heavy chain

<400> SEQUENCE: 3

gcactgaagc ttgtcctgat tgcctcagcc ttcagttttc aaatccagtc agtggtcatc     60
cctgaaaaca gacctttcac catgaagttg tggctgaact ggattttcct tctaacactt    120
ttaaaagata tccagtgtga ggtgaagctg ttggaatctg gaggaggttt ggtacagccg    180
gggggttctc tgagactctc ctgtgcagct tctggattca ccttcaatga tttctacatg    240
aactggatcc gccagcctcc agggcaggca cctgagtggt tgggtgttat tagaaacaaa    300
ggtaatggtt acacaacaga ggtcaataca tctgtgaagg ggcggttcac catctccaga    360
gataataccc aaaacatcct ctatcttcaa atgaacagcc tgagagctga ggacaccgcc    420
atttactact gtgcaagagg cggtccttat tactacagtg gtgacgacgc cccttactgg    480
ggccaaggag tcatggtcac agtctcctca gccaaaacaa cagccccatc ggtataccca    540
ctggcccctg tgtgtggaga tacaactggc tcctcggtga ctctaggatg cctggtcaag    600
ggttatttcc ctgagccagt gaccttgacc tggaactctg gatccctgtc cagtggtgtg    660
cacaccttcc cagctgtcct gcagtctgac ctctacaccc tcagcagctc agtgactgta    720
acctcgagca cctggcccag ccagtccatc acctgcaatg tggcccaccc ggcaagcagc    780
accaaggtgg acaagaaaat tgagcccaga gggcccacaa tcaagccctg tcctccatgc    840
aaatgcccag cacctaacct cttgggtgga ccatccgtct tcatcttccc tccaaagatc    900
aaggatgtac tcatgatctc cctgagcccc atagtcacat gtgtggtggt ggatgtgagc    960
gaggatgacc cagatgtcca gatcagctgg tttgtgaaca acgtggaagt acacacagct   1020
cagacacaaa cccatagaga ggattacaac agtactctcc gggtggtcag tgccctcccc   1080
atccagcacc aggactggat gagtggcaag gagttcaaat gcaaggtcaa caacaaagac   1140
ctcccagcgc ccatcgagag aaccatctca aaacccaaag ggtcagtaag agctccacag   1200
gtatatgtct tgcctccacc agaagaagag atgactaaga aacaggtcac tctgacctgc   1260
atggtcacag acttcatgcc tgaagacatt tacgtggagt ggaccaacaa cgggaaaaca   1320
gagctaaact acaagaacac tgaaccagtc ctggactctg atggttctta cttcatgtac   1380
agcaagctga gagtggaaaa gaagaactgg gtggaaagaa atagctactc ctgttcagtg   1440
gtccacgagg gtctgcacaa tcaccacacg actaagagct tctcccaaac tccgggtaaa   1500
ggaggtggtg gagggggagg cggtcaaggc ccaggggcac cacaggggcc tggtgcccca   1560
caaggaccgg gtgctcctca gggacccggg gcgccccaac agccgccaca gcaacccccca  1620
caacagcctc cgcaacaacc accgcagcag ccccctggag gtggtggatc cggtggaggg   1680
ggaagtggag gtggagggtc tcatatccac ggatgcgaca aaaatcactt gagagagatc   1740
atcggcattt tgaacgaggt cacaggagaa gggacgccat gcacggagat ggatgtgcca   1800
aacgtcctca cagcaacgaa gaacaccaca gagagtgagc tcgtctgtag ggcttccaag   1860
gtgcttctca tattttattt aaaacatggg aaaactccat gcttgaagaa gaactctagt   1920
gttctcatgg agctgcagag actctttcgg gcttttcgat gcctggattc atcgataagc   1980
tgcaccatga atgagtccaa gtccacatca ctgaaagact tcctggaaag cctaaagagc   2040
atcatgcaaa tggattactc gtagtctaga                                    2070
```

```
<210> SEQ ID NO 4
<211> LENGTH: 1914
<212> TYPE: DNA
<213> ORGANISM: Artificial Sequence
<220> FEATURE:
<223> OTHER INFORMATION: Nucleotide sequence of PyTh2 heavy chain

<400> SEQUENCE: 4

gcactgaagc ttgtcctgat tgcctcagcc ttcagttttc aaatccagtc agtggtcatc      60

cctgaaaaca gacctttcac catgaagttg tggctgaact ggattttcct tctaacactt     120

ttaaaagata tccagtgtga ggtgaagctg ttggaatctg gaggaggttt ggtacagccg     180

gggggttctc tgagactctc ctgtgcagct tctggattca ccttcaatga tttctacatg     240

aactggatcc gccagcctcc agggcaggca cctgagtggt tgggtgttat tagaaacaaa     300

ggtaatggtt acacaacaga ggtcaataca tctgtgaagg ggcggttcac catctccaga     360

gataataccc aaaacatcct ctatcttcaa atgaacagcc tgagagctga ggacaccgcc     420

atttactact gtgcaagagg cggtccttat tactacagtg gtgacgacgc cccttactgg     480

ggccaaggag tcatggtcac agtctcctca gccaaaacaa cagccccatc ggtataccca     540

ctggccccctg tgtgtggaga tacaactggc tcctcggtga ctctaggatg cctggtcaag     600

ggttatttcc ctgagccagt gaccttgacc tggaactctg gatccctgtc cagtggtgtg     660

cacaccttcc cagctgtcct gcagtctgac ctctacaccc tcagcagctc agtgactgta     720

acctcgagca cctggcccag ccagtccatc acctgcaatg tggcccaccc ggcaagcagc     780

accaaggtgg acaagaaaat tgagcccaga gggcccacaa tcaagccctg tcctccatgc     840

aaatgcccag cacctaacct cttgggtgga ccatccgtct tcatcttccc tccaaagatc     900

aaggatgtac tcatgatctc cctgagcccc atagtcacat gtgtggtggt ggatgtgagc     960

gaggatgacc cagatgtcca gatcagctgg tttgtgaaca acgtggaagt acacacagct    1020

cagacacaaa cccatagaga ggattacaac agtactctcc gggtggtcag tgccctcccc    1080

atccagcacc aggactggat gagtggcaag gagttcaaat gcaaggtcaa caacaaagac    1140

ctcccagcgc ccatcgagag aaccatctca aaacccaaag ggtcagtaag agctccacag    1200

gtatatgtct tgcctccacc agaagaagag atgactaaga aacaggtcac tctgacctgc    1260

atggtcacag acttcatgcc tgaagacatt tacgtggagt ggaccaacaa cgggaaaaca    1320

gagctaaact acaagaacac tgaaccagtc ctggactctg atggttctta cttcatgtac    1380

agcaagctga gagtggaaaa gaagaactgg gtggaaagaa atagctactc ctgttcagtg    1440

gtccacgagg gtctgcacaa tcaccacacg actaagagct tctcccaaac tccgggtaaa    1500

ggaggtggtg gatccggtgg agggggaagt ggaggtggag ggtctcatat ccacggatgc    1560

gacaaaaatc acttgagaga gatcatcggc attttgaacg aggtcacagg agaagggacg    1620

ccatgcacgg agatggatgt gccaaacgtc ctcacagcaa cgaagaacac cacagagagt    1680

gagctcgtct gtagggcttc caaggtgctt ctcatatttt atttaaaaca tgggaaaact    1740

ccatgcttga agaagaactc tagtgttctc atggagctgc agagactctt tcgggctttt    1800

cgatgcctgg attcatcgat aagctgcacc atgaatgagt ccaagtccac atcactgaaa    1860

gacttcctgg aaagcctaaa gagcatcatg caaatggatt actcgtagtc taga          1914


<210> SEQ ID NO 5
<211> LENGTH: 849
<212> TYPE: DNA
<213> ORGANISM: Artificial Sequence
<220> FEATURE:
```

<223> OTHER INFORMATION: Nucleotide sequence of the chimeric Ig-kappa

<400> SEQUENCE: 5

```
agaagttact ctcagtgaag atatagcatc aacatcagag ttctccctga gcttctgggg     60
ctgctgttac tctggttttc tggtgtgaga tgtgacatcc agatgacaca gtctccgtca    120
tttctgtcta catctcttgg aaacagcatc accatcactt gccatgccag tcagaacatc    180
aagggttggt tagcctggta ccaacaaaag tcagggaatg ctcctcaact gttgatttat    240
aaggcatcta gcctgcaatc aggggttcca tcaagattca gtggcagtgg atctggaaca    300
gattatattt tcactatcag caacctacag cctgaagata ttgccactta ttactgtcag    360
cattatcaaa gctttccgtg gacgttcggt ggaggcacca agctggaatt gaaacgggat    420
gctgcaccaa ctgtatccat cttcccacca tccagtgagc agttaacatc tggaggtgcc    480
tcagtcgtgt gcttcttgaa caacttctac cccaaagaca tcaatgtcaa gtggaagatt    540
gatggcagtg aacgacaaaa tggcgtcctg aacagttgga ctgatcagga cagcaaagac    600
agcacctaca gcatgagcag caccctcacg ttgaccaagg acgagtatga acgacataac    660
agctatacct gtgaggccac tcacaagaca tcaacttcac ccattgtcaa gagcttcaac    720
aggaatgagt gtggaggtgg tggatccggt ggagggggaa tgggaggtgg agggtcttac    780
aatcgaaata tagtcaacag attacttggc gatgctctca acggaaaacc agaagaaaaa    840
tgatctaga                                                            849
```

<210> SEQ ID NO 6
<211> LENGTH: 33
<212> TYPE: DNA
<213> ORGANISM: Artificial Sequence
<220> FEATURE:
<223> OTHER INFORMATION: Th1-Fg1-F primer

<400> SEQUENCE: 6

```
gcactgaagc ttgtcctgat tgcctcagcc ttc                                  33
```

<210> SEQ ID NO 7
<211> LENGTH: 51
<212> TYPE: DNA
<213> ORGANISM: Artificial Sequence
<220> FEATURE:
<223> OTHER INFORMATION: Th1-Fg1-F primer

<400> SEQUENCE: 7

```
cagtgggtat accgatgggg ctgttgtttt ggctgaggag actgtgacca t              51
```

<210> SEQ ID NO 8
<211> LENGTH: 25
<212> TYPE: DNA
<213> ORGANISM: Artificial Sequence
<220> FEATURE:
<223> OTHER INFORMATION: Th1-Fg2-F primer

<400> SEQUENCE: 8

```
ccatcggtat acccactggc ccctg                                           25
```

<210> SEQ ID NO 9
<211> LENGTH: 28
<212> TYPE: DNA
<213> ORGANISM: Artificial Sequence
<220> FEATURE:
<223> OTHER INFORMATION: Ch1-R primer

<400> SEQUENCE: 9
gattgtgggc cctctgggct caattttc 28

<210> SEQ ID NO 10
<211> LENGTH: 31
<212> TYPE: DNA
<213> ORGANISM: Artificial Sequence
<220> FEATURE:
<223> OTHER INFORMATION: IgG2aFc-F primer

<400> SEQUENCE: 10
cagagggccc acaatcaagc cctgtcctcc a 31

<210> SEQ ID NO 11
<211> LENGTH: 99
<212> TYPE: DNA
<213> ORGANISM: Artificial Sequence
<220> FEATURE:
<223> OTHER INFORMATION: PyB-F primer

<400> SEQUENCE: 11
agggccccgg ggcgccccaa gagccgccac agcaaccccc acaacagcct ccgcaacaac 60
caccgcagca gccccctgga ggtggtggat ccggtggag 99

<210> SEQ ID NO 12
<211> LENGTH: 67
<212> TYPE: DNA
<213> ORGANISM: Artificial Sequence
<220> FEATURE:
<223> OTHER INFORMATION: PyB-1R primer

<400> SEQUENCE: 12
cccctgtggt gcccctgggc cttgaccgcc tccccctcca ccacctcctt tacccggagt 60
ccgggag 67

<210> SEQ ID NO 13
<211> LENGTH: 79
<212> TYPE: DNA
<213> ORGANISM: Artificial Sequence
<220> FEATURE:
<223> OTHER INFORMATION: PyB-2R primer

<400> SEQUENCE: 13
gcgccccggg tccctgagga gcacccggtc cttgtggggc accaggcccc tgtggtgccc 60
ctgggccttg accgcctcc 79

<210> SEQ ID NO 14
<211> LENGTH: 59
<212> TYPE: DNA
<213> ORGANISM: Artificial Sequence
<220> FEATURE:
<223> OTHER INFORMATION: B7.1-F primer

<400> SEQUENCE: 14
ggtggtggat ccggtggagg gggaagtgga ggtggagggt ctgttgatga acaactgtc 59

<210> SEQ ID NO 15
<211> LENGTH: 31
<212> TYPE: DNA
<213> ORGANISM: Artificial Sequence
<220> FEATURE:
<223> OTHER INFORMATION: B7.1-R primer

<400> SEQUENCE: 15

-continued

```
tgcatctaga tcacttgcta tcaggagggt c                               31


<210> SEQ ID NO 16
<211> LENGTH: 60
<212> TYPE: DNA
<213> ORGANISM: Artificial Sequence
<220> FEATURE:
<223> OTHER INFORMATION: IL-4-F primer

<400> SEQUENCE: 16

ggtggtggat ccggtggagg gggaagtgga ggtggagggt ctcatatcca cggatgcgac     60


<210> SEQ ID NO 17
<211> LENGTH: 33
<212> TYPE: DNA
<213> ORGANISM: Artificial Sequence
<220> FEATURE:
<223> OTHER INFORMATION: IL-4-R primer

<400> SEQUENCE: 17

cctcctctag actacgagta atccatttgc atg                             33


<210> SEQ ID NO 18
<211> LENGTH: 21
<212> TYPE: PRT
<213> ORGANISM: Artificial Sequence
<220> FEATURE:
<223> OTHER INFORMATION: PyCSP CD4 T cell epitope

<400> SEQUENCE: 18

Tyr Asn Arg Asn Ile Val Asn Arg Leu Leu Gly Asp Ala Leu Asn Gly
1               5                   10                  15

Lys Pro Glu Glu Lys
            20


<210> SEQ ID NO 19
<211> LENGTH: 44
<212> TYPE: PRT
<213> ORGANISM: Artificial Sequence
<220> FEATURE:
<223> OTHER INFORMATION: PyCSP B cell repeats

<400> SEQUENCE: 19

Gln Gly Pro Gly Ala Pro Gln Gly Pro Gly Ala Pro Gln Gly Pro Gly
1               5                   10                  15

Ala Pro Gln Gly Pro Gly Ala Pro Gln Gln Pro Pro Gln Gln Pro Pro
            20                  25                  30

Gln Gln Pro Pro Gln Gln Pro Pro Gln Gln Pro Pro
        35                  40
```

TH1/TH2 POLARIZING VACCINES

CROSS-REFERENCE TO RELATED APPLICATIONS

This application claims priority to U.S. Provisional Application No. 61/284,357, filed Nov. 16, 2009.

FIELD OF INVENTION

The present invention relates to recombinant chimeric molecules that may be used as a whole or a component of a vaccine. More specifically, this invention relates to chimeric molecules that are capable of providing T cell receptor (TCR) interaction as well as co-stimulation of T cells. Both interactions are required for activation and differentiation of pathogen-specific T cells. The chimeric molecules may also be capable of elicit antibodies against pathogen-specific B cell epitope(s).

BACKGROUND OF THE INVENTION

Malaria is a vector-borne infectious disease caused by a eukaryotic protist of the genus *Plasmodium*. It is widespread in tropical and subtropical regions, including parts of the Americas, Asia, and Africa. Each year 350-500 million cases of malaria occur worldwide, and over one million people die, most of them young children (Malaria facts, Center for Disease Control and Prevention. As anti-vector and anti-parasite approaches failed due to resistance to pesticides or resistance to anti-parasite drugs, research efforts began to focus on malaria vaccine development as an effective and inexpensive alternative approach.

Current malaria vaccines are made of attenuated or killed whole pathogens, subunits in the form of purified proteins, peptides, or recombinant DNA that is artificially integrated into living vehicles, such as a viral vector (i.e, adenovirus, vaccinia virus etc.). However, the complex parasitic life cycle has confounded the efforts to develop efficacious vaccines for malaria. Malaria's parasitic life cycle is divided between the mosquito (the insect host) and the human host. While in the human host, it passes through several developmental stages in different organellar environments, including the liver stage and the blood stage. Antigen diversity is a characteristic that must be taken into account in malaria vaccine development, which includes a high degree of developmental stage specificity, antigenic variation and antigen polymorphism. This means different stages of the parasite may require different immune mechanisms for protection.

Vaccine candidates have been identified from each of the parasite's developmental stages.

RTS,S is one candidate entering large scale efficacy trials in Africa, that offers partial protection against infection and clinical disease. Based on the dominant surface protein of the sporozoite (circumsporrozoite protein or CSP), RTS,S is the only subunit vaccine that has consistently demonstrated protection. Recombinant protein vaccines based on other antigens, including thrombospondin related adhesive protein/sporozoite surface protein-2 (TRAP/SSP2), liver stage antigen-1 (LSA1), merozoite surface protein-1 (MSP1), apical membrane antigen-1 (AMA-1), and others have not shown protection to date in experimental sporozoite challenge studies in humans or in field trials in endemic areas. However, in some cases, strain-specific protective effects have been observed.

Faced with limited success, vaccine developers have turned to novel vaccine platforms, such as viral vectors and heterologous prime/boost approaches. With these new approaches, success has been even more modest, with only one of 35 volunteers sterilely protected by a heptavalent poxvirus vaccine called NYVACPf7 and a similar proportion sterilely protected with prime/boost vaccines based on MVA and fowl pox. DNA plasmid vaccines have been particularly disappointing (1).

Some intracellular pathogens such as viruses need strong inflammatory (Th1) responses in order to be cleared. On the other hand, worm parasites and toxin-producing bacteria require anti-inflammatory (Th2) responses for effective neutralization and clearance. Though this follows a general rule still there are infectious agents such as malaria or HIV for which we still do not know the type of immune response required for protection. It is believed that immune evasion induced by the parasite has contributed to the limited success of subunit malaria vaccines.

In order to survive and induce infection, many infectious organisms have developed mechanisms to evade the immune system. One common mechanism is the inhibition of expression of costimulatory ligands on APCs that leads to T cell tolerance to the nominal pathogen [12] Malaria vaccines administered to a subject need to be taken up by immune competent cells, such as antigen-presenting cells ("APCs") so the immunogenic subunits are processed and degraded into peptides, which are then presented to the T cells in the context of Major Histocompatibility Molecules (MHC). The T cells recognize the MHC-peptide complexes through the T cell receptor (TCR). TCR interaction with MHC-peptide complexes induces early signaling in T cells for activation. However, T cells require two signals to become fully activated. A first signal, which is antigen-specific, is provided through the T cell receptor which interacts with peptide-MHC molecules on the membrane of antigen presenting cells (APC). A second signal, the costimulatory signal, is antigen nonspecific, and is provided by the interaction between costimulatory molecules expressed on the membrane of APC and the T cell. The failure of APCs to provide co-stimulation leads to a state of T cell tolerance to the presented antigens/peptides (11).

Research has been conducted to genetically engineer chimeric proteins with functional properties to allow manipulation of the immune system [3-6, 8-10]. An example of it is shown in U.S. Pat. No. 6,811,785 and US Pub No. 20040234531. However, none of the current approaches present molecule that can provide antigenic as well as costimulatory signals to the immune system. Our genetically engineered chimeric proteins may offer a novel vaccine platform to overcome the T cell tolerance induced by pathogens for treatment or prevention of a human disease.

DETAILED DESCRIPTION OF THE INVENTION

Figure 1:
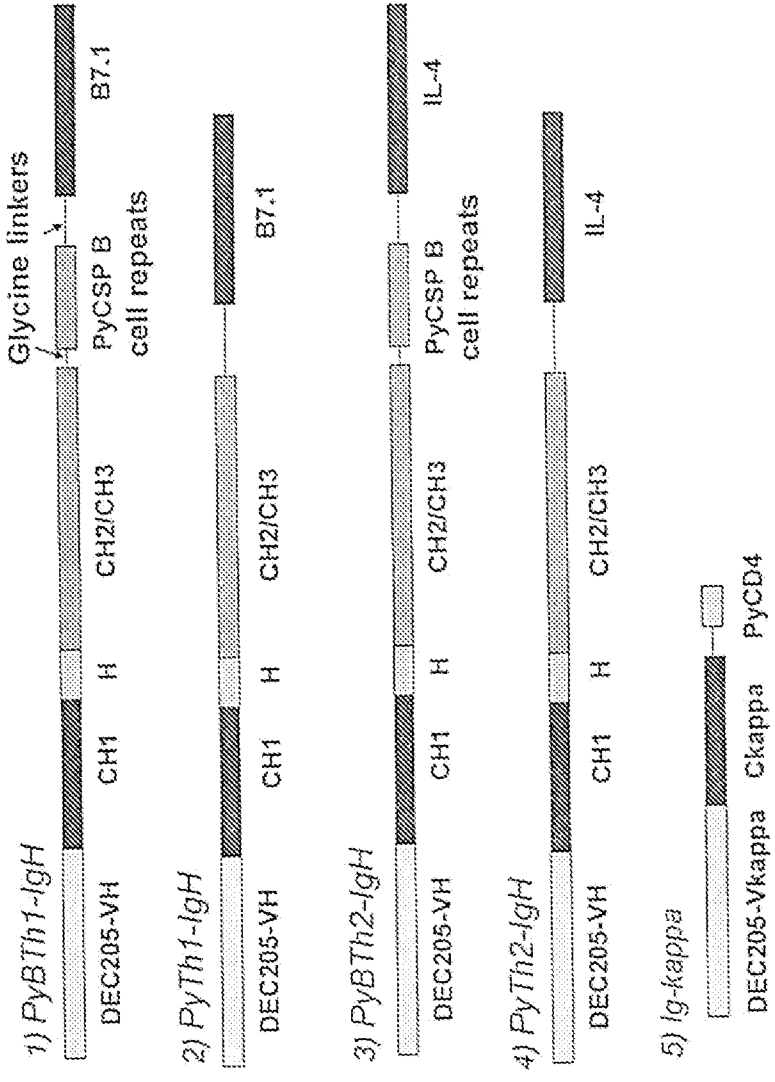
FIG. 1. Genetic construction of chimeric Ig-H and Ig-kappa genes encoding for Th1/Th2-polarizing vaccines. Each vaccine, namely PyBTh1, PyTh1, PyBTh2, and PyTh2 are encoded by a specific Ig-H gene and a common Ig-kappa gene. Schematic representation of the chimeric genes is shown. Each genetic domain is represented by boxes. Flexible glycine linkers between domains are indicated by lines.

An aspect of this invention is chimeric molecules capable of providing TCR interaction and costimulation required for full activation and differentiation of pathogen-specific T cells. The chimeric molecules may also elicit antibodies against pathogen-specific B cell epitope(s).

Another aspect of this invention is a vaccine platform that enables a subject's immune system to overcome T cell tolerance induced by malarial pathogens.

Yet another aspect of this invention is a method of making a malaria vaccine comprising chimeric molecules enables a subject's immune system to overcome T cell tolerance induced by malarial pathogens.

A further aspect of this invention is a method for inducing an immune response against malaria using genetically engineered chimeric molecules capable of providing TCR interaction and costimulation required for full activation and differentiation of pathogen-specific CD4 T cells.

General Structure of Chimeric Molecules

The chimeric molecule of this invention is referred to herein as a protein, however, such "chimeric proteins" as defined herein may comprise non-protein components, including but not limited to, carbohydrate residues, chemical crosslinking agents, lipids, etc.

An embodiment of the present invention is a chimeric molecule comprising an immunoglobulin scaffold with specificity for an antigen presenting cell and expressing critical components for activation of a T cells and/or B cells. The use of so-called protein scaffolds or immunoglobulin scaffold has recently attracted considerable attention in biochemistry in the context of generating novel types of ligand receptors for various applications in research and medicine. This development started with the notion that immunoglobulins owe their function to the composition of a conserved framework region and a spatially well-defined antigen-binding site made of peptide segments that are hypervariable both in sequence and in conformation. Laboratories exploit different types of protein architectures for the construction of practically useful binding proteins. Properties like small size of the receptor protein, stability and ease of production were the focus of this work. Hence, among others, single domains of antibodies or of the immunoglobulin superfamily, protease inhibitors, helix-bundle proteins, disulphide-knotted peptides and lipocalins were investigated. In an embodiment of this invention, the chimeric molecule comprises a costimulatory domain linked to the heavy chain of an immunoglobulin scaffold and a pathogen-specific T cell epitope linked to the light chain of the immunoglobulin scaffold. A pathogen-specific B Cell epitope may also be linked to the heavy chain of the immunoglobulin scaffold.

The immunoglobulin scaffold for the chimeric molecule may comprise domains of any immunoglobulin found in human, including but not limited to IgG1, IgG2, IgG3, IgG4, IgM, IgA1, IgA2 and IgE. For example, IgG antibodies are large tetrameric quaternary molecules of about 150 kDa, composed of four peptide chains, including two identical heavy chains of about 50 kDa and two identical light chains of about 25 kDa. The two heavy chains are linked to each other and to a light chain by disulfide bonds. The resulting tetramer has two identical halves, which together form the Y-like shape. Each end of the fork contains an identical antigen binding site.

The immunoglobulin scaffold of this invention has specificity to bind to marker of an antigen presenting cell, such as a Dendritic cell, Langerhans cells, B cells, monocyte, macrophage, endothelial cells, or granulocytes. Examples of genes that encode an epitope for binding to an antigen-presenting cell may include but not limited to CD205, CD11b, CD11c, CD14, and CD19. In a non-limiting embodiment of this invention, the domain of the constant region of IgG2a is used for the construction of the immunoglobulin scaffold, wherein said immunoglobulin is humanized and has specificity for a dendritic cell marker, such as DEC205.

The costimulatory domain of a chimeric molecule of this invention may include but not limited to B7.1 (CD80), B7.2 (CD86), Interleukin 2, Interleukin 12, interleukin 23, interleukin-6, which stimulate the CD4 T cells to differentiate into effector Th1 cells. The costimulatory domain, may also include but not limited to interleukin-4, interleukin-5, interleukin-10, interleukin-17 or interleukin-13, which stimulate the CD4 T cells to differentiate of effector Th2 cells.

The pathogen-specific T cell epitope of a chimeric molecule of this invention may be a CD4 T cell epitope or a CD8 T cell epitope, and may comprise any epitope of a pathogenic antigen. In a non-limiting embodiment of this invention, malaria antigen including but not limited to circumsporrozoite protein (CSP), thrombospondin related adhesive protein/sporozoites surface protein-2 (TRAP/SSP2), liver stage antigen-1 (LSA1), merozoite surface protein-1 (MSP1), apical membrane antigen-1 (AMA-1). The chimera may also bear T cell epitopes from other infectious agents such as hepatitis B, influenza A or B, rabies, rotavirus, enteroviruses, HIV, enterobacterias, *Strepcococcus, Staphylococcus, toxoplasma, Leishmania.*

One or more pathogen-specific B cell epitope may be also linked to the C-terminus of the Immunoglobulin heavy chain. The pathogen-specific B cell epitope may comprise any malaria antigens or an epitope of a malaria antigen, including but not limited to circumsporrozoite protein (CSP), thrombospondin related adhesive protein/sporozoites surface protein-2 (TRAP/SSP2), liver stage antigen-1 (LSAT), merozoite surface protein-1 (MSP1), apical membrane antigen-1 (AMA-1). The chimera may also bear B cell epitopes from other infectious agents such as hepatitis B, influenza A or B, rabies, rotavirus, enteroviruses, HIV, enterobacterias, Strepcococcus, Staphylococcus, toxoplasma, Leishmania.

Figure 11A:
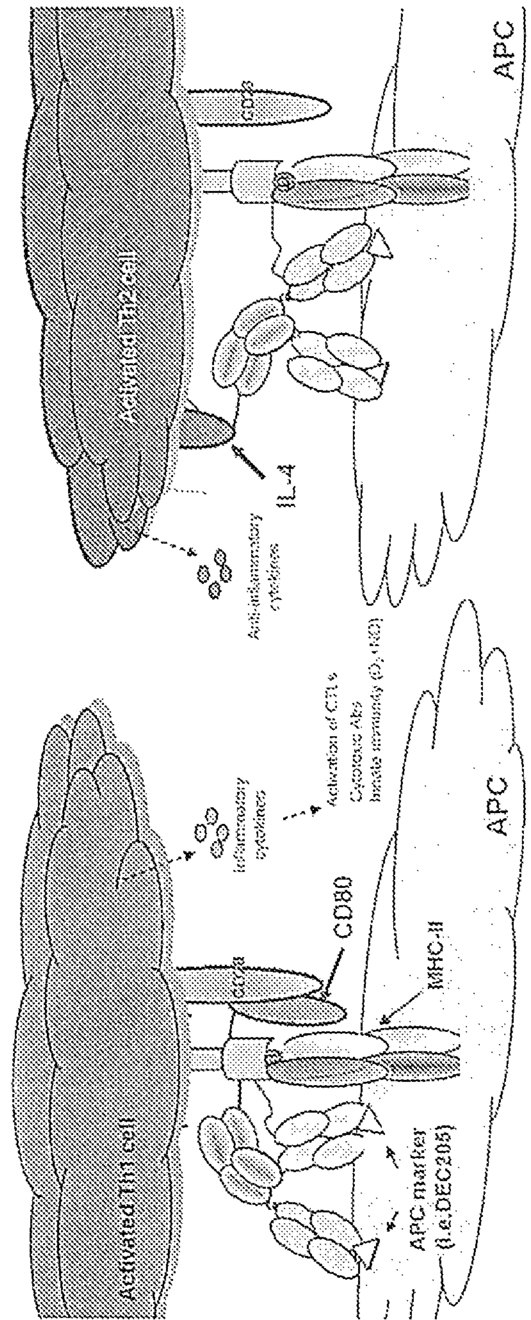
FIG. 11A Schematic representation of the chimeric molecules PyBTh1 and PyBTh2.
Figure 11B:
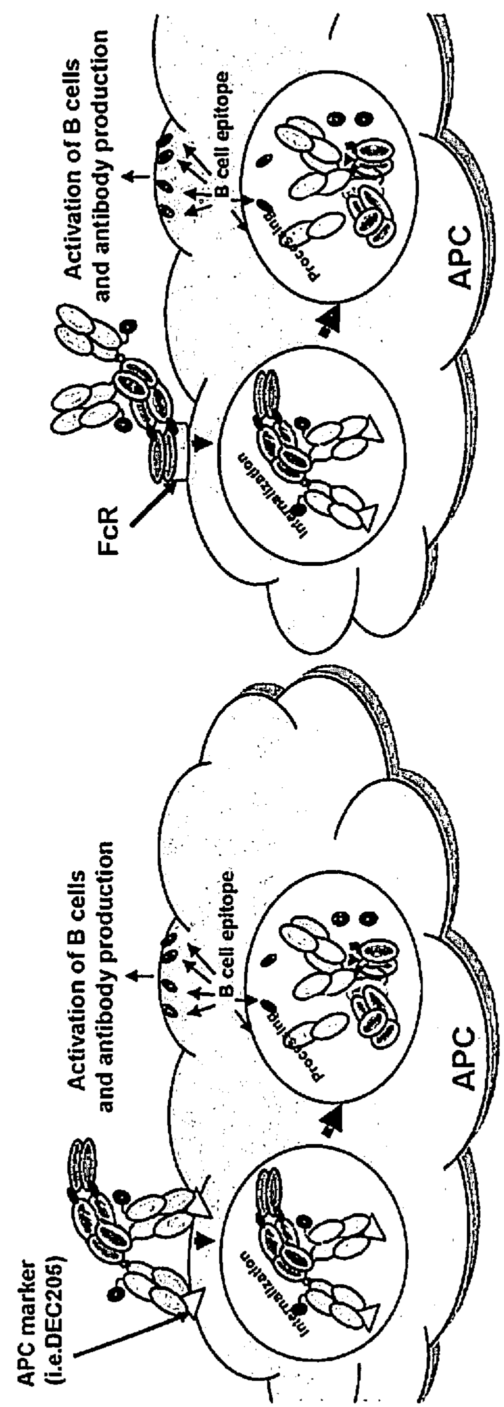
FIG. 11B Schematic representation of the mechanism of action of chimeric molecules PyBTh1 and PyBTh2.

The chimeric molecules of this invention may be used alone or together with other pharmaceutical composition in a vaccine. An illustration of the mechanisms of action of such a chimeric vaccine is illustrated in FIG. 11. The different parts of the chimeric molecules may be linked via linker, such as a glycine linker.

Example 1: Genetic Construction of Chimeric Ig-H and Ig-Kappa Genes

Four chimeric molecules were made using genetic engineering techniques, and are separately designated as PyTh1, PyBTh1, PyTh2 and PyBTh2. Each chimera vaccine molecule is encoded by two genes. One gene encodes a specific heavy chain of the immunoglobulin (Ig-H gene) of each vaccine molecule. A second gene encodes the Kappa light chain of the immunoglobulin, which is common among the four chimeric molecules (Ig-kappa gene). Genetic sequences encoding the Ig-H of each chimeric molecule were shown in Table 1.

As shown in FIG. 1 (1) and (3), the chimeric Ig-H genes of PyBTh1 and PyBTh2 contain regions encode for the variable region of rat anti-mouse DEC205 (VH), mouse IgG2a components (CH1, hinge, CH2 and CH3), PyCSP B cell repeats $[QGPGAP]_4[QQPP]_5$ and a T cell costimulatory ligand. The T cell costimulatory ligand is B7.1 for chimeric molecule PyBTh1 or IL-4 for chimeric molecule PyBTh2.

As shown in FIG. 1 (2) and (4), the chimeric Ig-H genes of PyTh1 and PyTh2 lack the sequence encoding for the PyCSP B cell repeats. The T cell costimulatory ligand for chimeric molecule PyTh1 is B7.1 and the T cell costimulatory ligand for chimeric molecule PyTh2 is IL-4.

The chimeric Ig-kappa gene shown in FIG. 1 (5), encodes for the Ig-kappa variable region of rat anti-mouse DEC-205 (VL), mouse constant Ckappa domain, and the $PyCSP_{59-79}$ immunodominant CD4 T cell epitope recognized by T cells in the context of $H\text{-}2^d$ class II molecules.

The genes encoding for rat anti-DEC205 Ig-variable domain (VH+VL) were cloned by rapid amplification of cDNA ends (RACE) using mRNA from rat anti-mouse DEC205 hybridoma cells (ATCC). Genes encoding for the constant domains of mouse Fc gamma and Ckappa, and the mouse costimulatory ligands (B7.1 and IL-4) were cloned by RT-PCR from mRNA extracted from BALB/c splenic cells. Sequences encoding for the PyCSP CD4 T epitope (SEQ ID NO. 18) and PyCSP B cell repeats $[[QGPGAP]_4[QQPP]_5]$ (SEQ ID NO. 19) were inserted into the chimeric genes by site directed mutagenesis. Primers used for the genetic construction are shown in Table 2. The chimeric Ig-H and Ig-kappa genes were cloned under the CMV promoter in pCDNA3/Zeo (INVITROGEN®, San Diego, Calif.) and pcDNA/Neo plasmids (INVITROGEN®, San Diego, Calif.), respectively. Nucleotide sequencing revealed that the various components of the chimeric genes were "in frame" and do not bear mutations.

TABLE 1

Genes encoding the chimeric molecules

| Chimeric Molecule Subunit | Nucleotide Sequences |
|---|---|
| Phy-B-Th1(IgH) | SEQ ID NO. 1 |
| PhyTh1(IgH) | SEQ ID NO. 2 |
| Phy-B-Th1(IgH) | SEQ ID NO. 3 |
| PhyTh2(IgH) | SEQ ID NO. 4 |
| Ig-kappa | SEQ ID NO. 5 |

Example 2: Expression of the Chimeric Th1/Th2 Genes in Stably Transfected Myeloma SP20 Cells The plasmids encoding for the chimeric Ig-H and Ig-k genes were doubly transfected into mouse myeloma SP20 cells. Stable transfectants were selected by resistance to G418 and zeocin. To rule out amplification of plasmid DNA, some samples were subjected to retrotranscription (RD and then amplified by PCR using specific primers set forth in table 2.

TABLE 2

Primers

| Primers | SEQ ID No. |
|---|---|
| Th1-Fg1-F: GCACTGAAGCTTGTCCTGATTGCCTCAGCCTTC | 6 |
| Th1-Fg1-R: CAGTGGGTATACCGATGGGGCTGTTGTTTTGGCTGAGGAGACTGTGACCAT | 7 |

TABLE 2-continued

| Primers | |
|---|---|
| Primers | SEQ ID No. |
| Th1-Fg2-F: CCATCGGTATACCCACTGGCCCCTG | 8 |
| CH1-R: GATTGTGGGCCCTCTGGGCTCAATTTTC | 9 |
| IgG2aFc-F: CAGAGGGCCCACAATCAAGCCCTGTCCTCCA | 10 |
| PyB-F: AGGGCCCCGGGGCGCCCCAAGAGCCGCCACAGCAACCCCCACAACAGCCTCC GCAACAACCACCGCAGCAGCCCCCTGGAGGTGGTGGATCCGGTGGAG | 11 |
| PyB-1R: CCCCTGTGGTGCCCCTGGGCTTGACCGCCTCCCCCTCCACCACCTCCTTTAC CCGGAGTCCGGGAG | 12 |
| PyB-2R (new): GCGCCCCGGGTCCCTGAGGAGCACCCGGTCCTTGTGGGGCACCAGGCCCCTG TGGTGCCCCT GGGCCTTGACCGCCTCC | 13 |
| B7.1-F: GGTGGTGGATCCGGTGGAGGGGGAAGTGGAGGTGGAGGGTCTGTTGATGAA CAACTGTC | 14 |
| B7.1-R: TGCATCTAGATCACTIGCTATCAGGAGGGTC | 15 |
| IL-4-F: GGTGGTGGATCCGGTGGAGGGGGAAGTGGAGGTGGAGGGTCTCATATCCACG GATGCGAC | 16 |
| IL-4-R: CCTCCTCTAGACTACGAGTAATCCATTTGCATG | 17 |

Figure 2A:
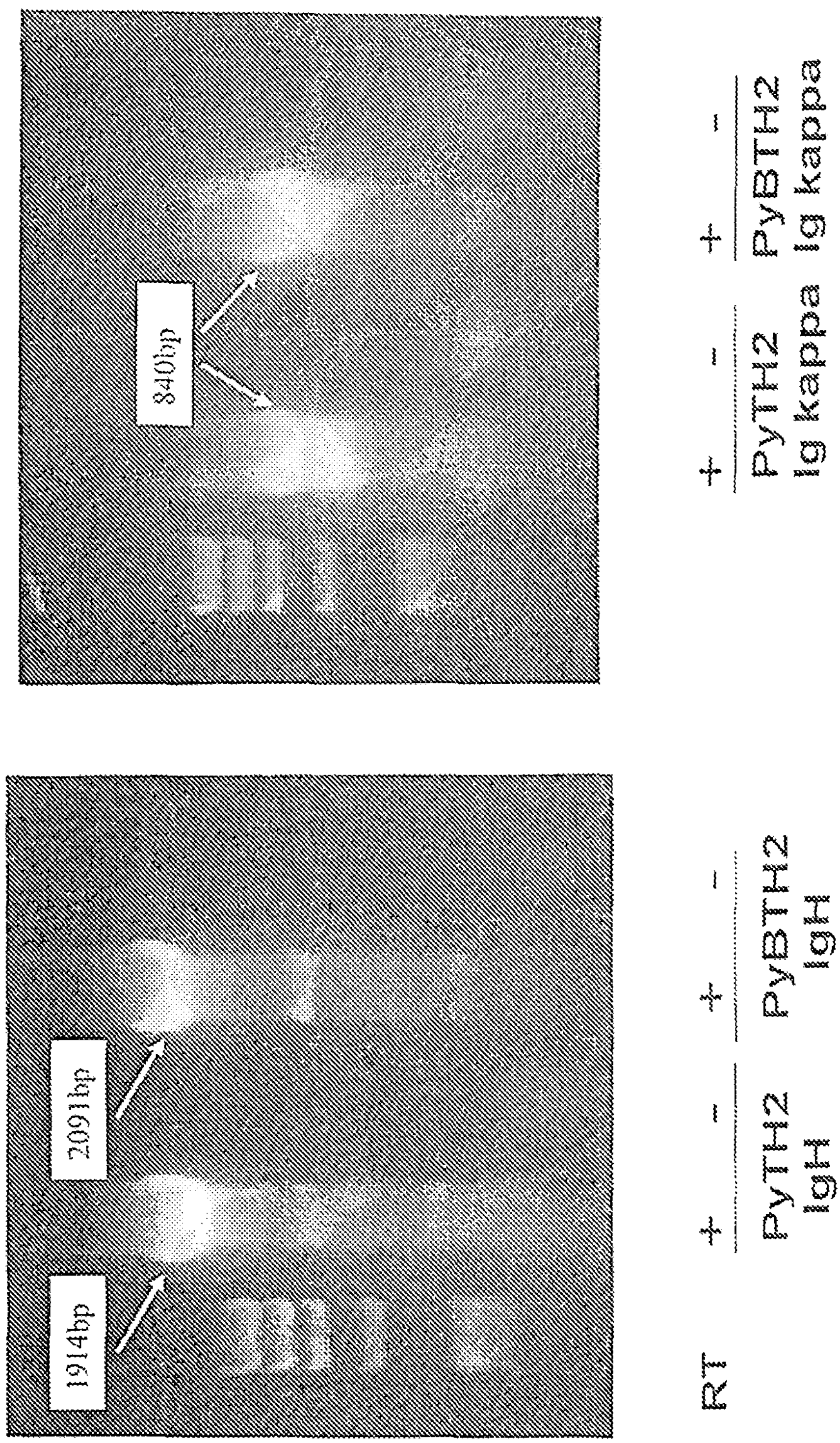
FIG. 2A. Expression of the chimeric Th1/Th2 genes in stably transfected myeloma SP20 cells. mRNA extracted from plasmid-transfected SP20 cells was used as template for RT-PCR amplification of the chimeric Ig-H (left panel) and Ig-kappa genes (right panel).
Figure 2:
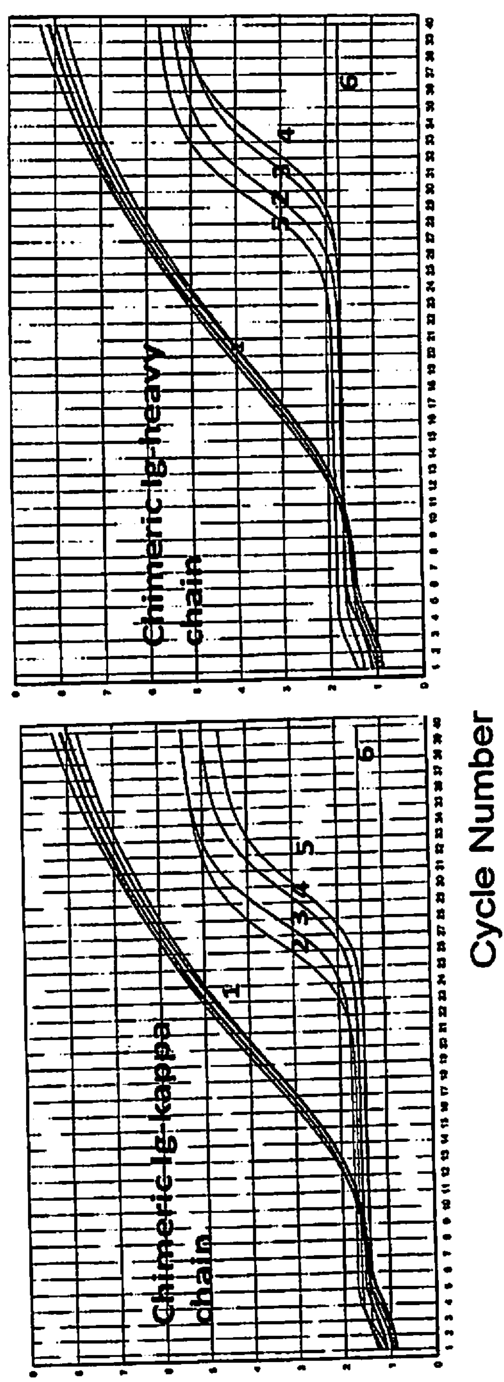
FIG. 2B. Expression of the chimeric Th1/Th2 genes in stably transfected myeloma SP20 cells. Expression of the chimeric Ig-H (right panel) and Ig-kappa (left panel) genes as measured by real-time RT-PCR. Expression of 18S RNA by transfected cells is also shown. Results indicate active transcription of the transfected genes encoding for the Th1/Th2 vaccines.

The chimeric proteins were purified from the cell culture supernantants by affinity chromatography using anti-mouse IgG columns. The yield of protein production is approximately 1 mg per liter of supernatant. The SP20 stable transfectants were showed to express the chimeric Ig-H and Ig-k genes, as measured by real-time PCR (FIG. 2A). Expression of the chimeric Ig-H (FIG. 2B right panel) and Ig-kappa (FIG. 2B left panel) genes were measured by real-time RT-PCR. Expression of 18S RNA by transfected cells is also shown FIG. 2. Results indicate active transcription of the transfected genes encoding for the Th1/Th2 vaccines.

Example 3: Immunocharacterization of Th1/Th2-Polarizing Vaccines

Figure 3A:
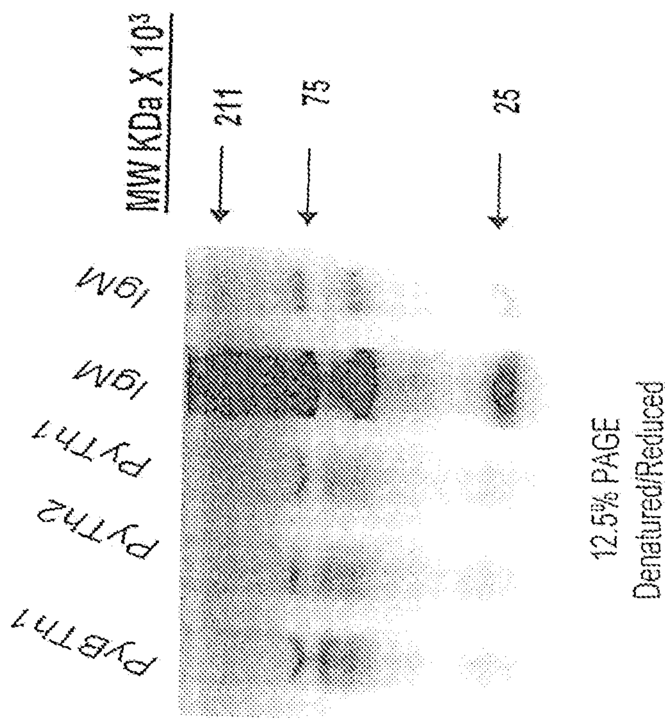
FIG. 3A. Immunocharacterization of Th1/Th2-polarizing vaccines. Silver stain gels showing the molecular size of the Th1/Th2 vaccines in denaturing (left panel) and denaturing/reducing conditions (right panel).
Figure 3A:
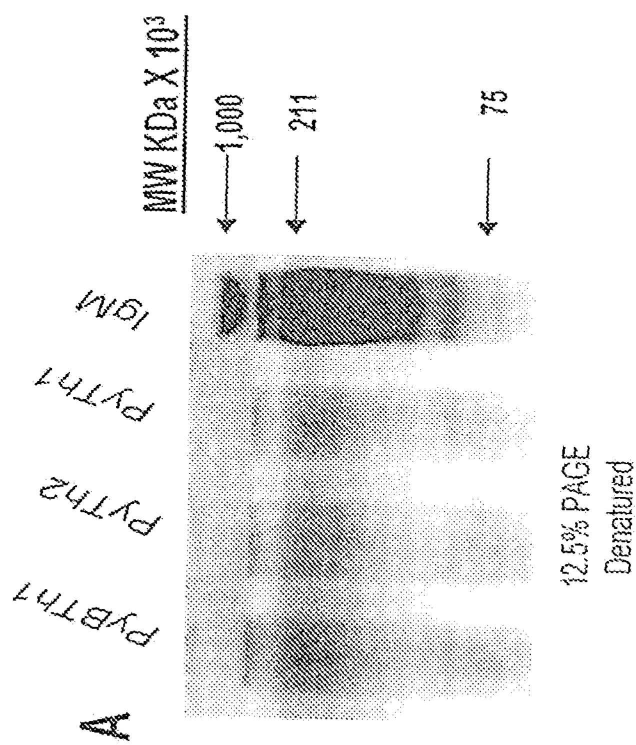
Figure 3B:
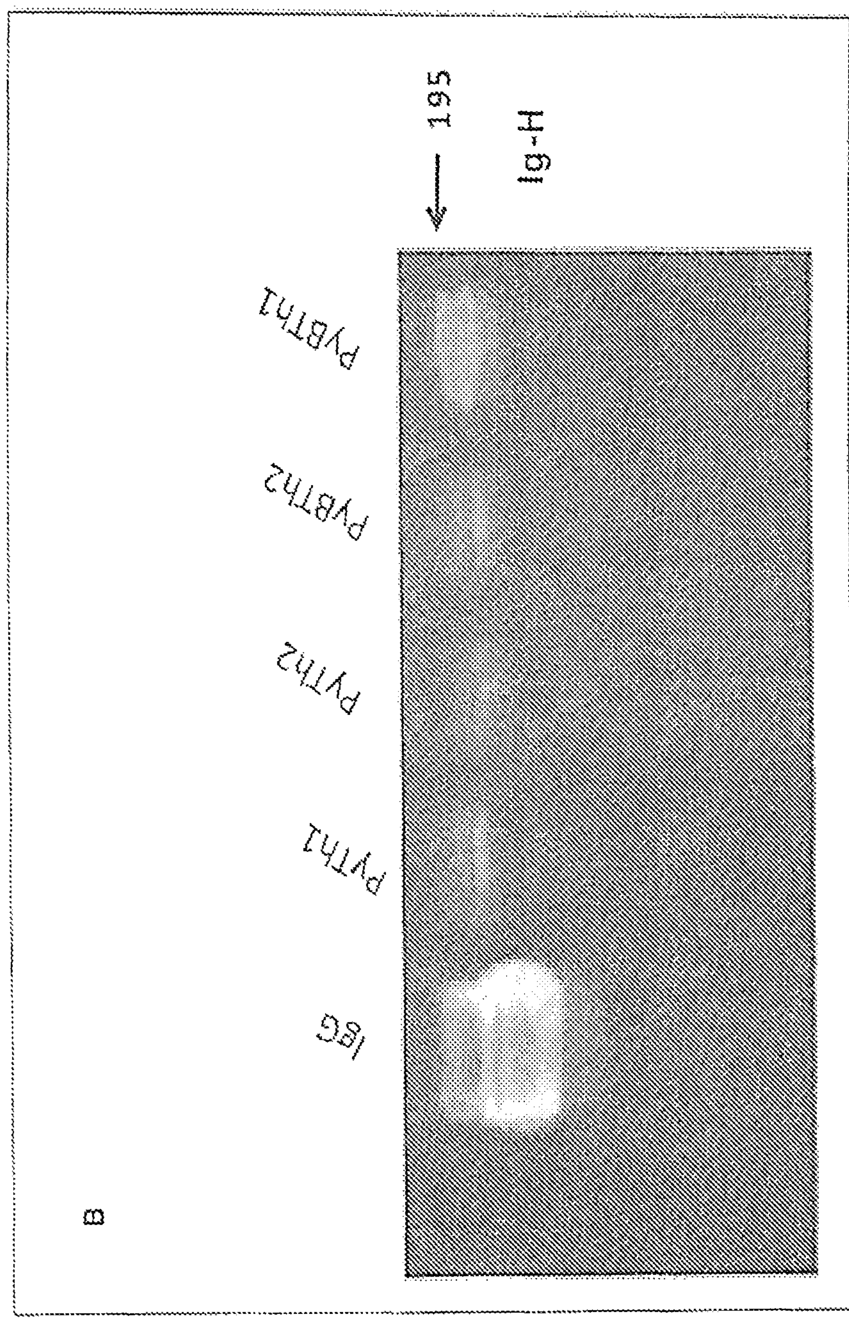
FIG. 3B. Immunocharacterization of Th1/Th2-polarizing vaccines. Western blotting of Th1/Th2-polarizing vaccines using anti-mouse IgG heavy chain.
Figure 3C:
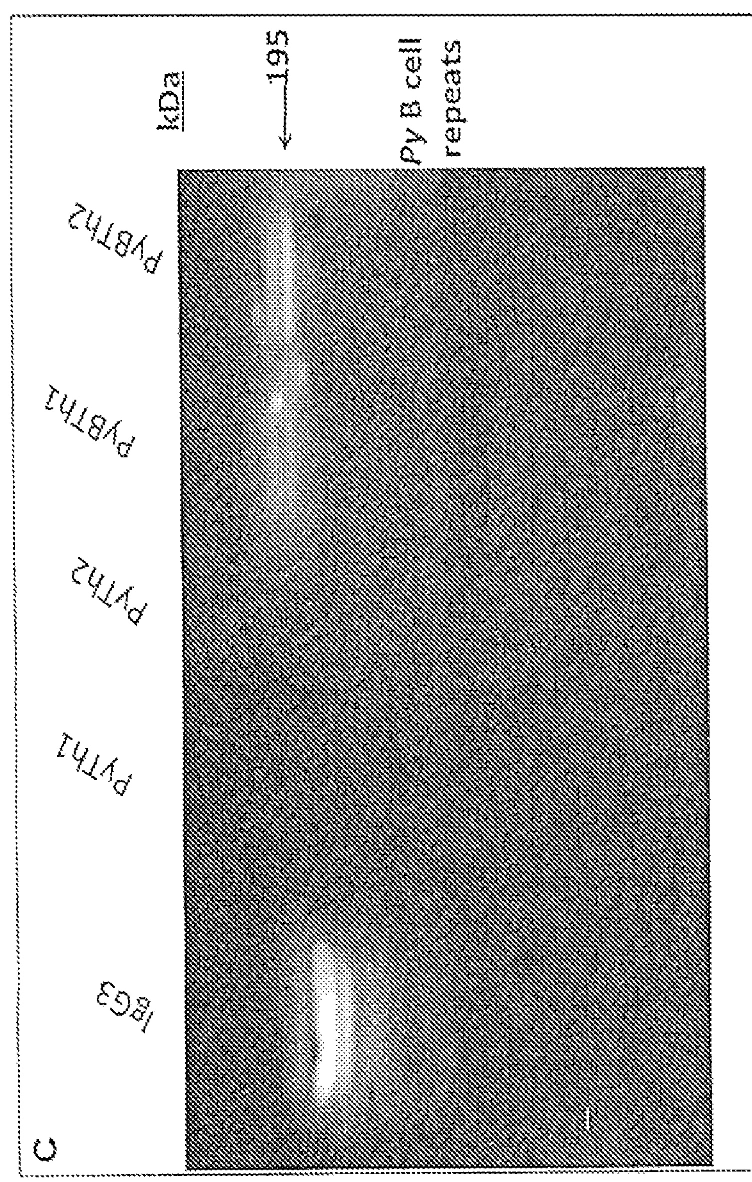
FIG. 3C. Immunocharacterization of Th1/Th2-polarizing-vaccines. Western blotting of Th1/Th2-polarizing vaccines using anti-PyCSP B cell repeats (NSLY) mAb.
Figure 3D:
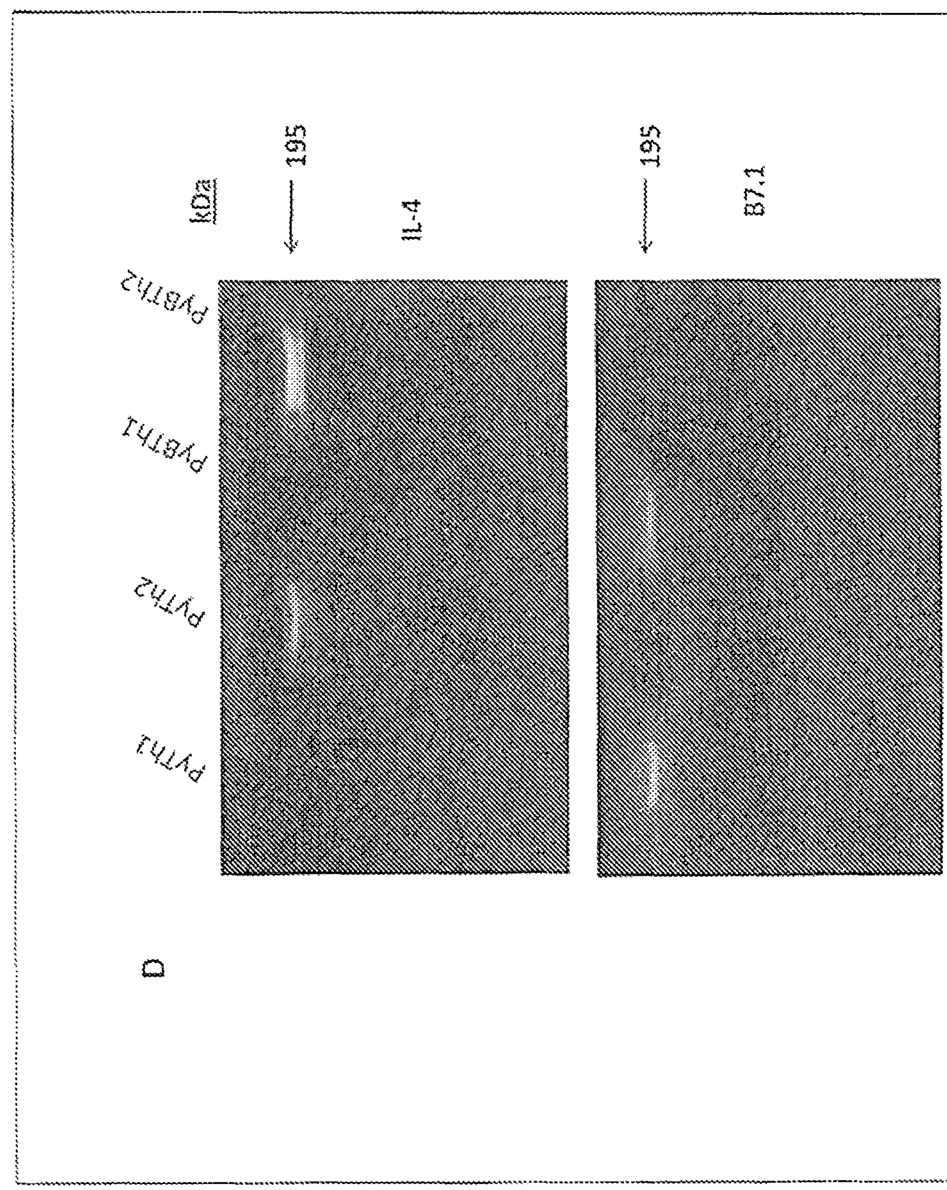
FIG. 3D. Immunocharacterization of Th1/Th2-polarizing vaccines. Western blotting of Th1/Th2-polarizing vaccines using anti-mouse IL-4 (upper panel) and anti-mouse B7.1 (CD80) (lower panel) mAbs.

The plasmid of the TH1/Th2 chimeric vaccines were purified from cell culture supernatants of plasmid-transfected SP20 cells by affinity-chromatography using anti-mouse IgG columns. Silver stain gels show the molecular size of the Th1/Th2 vaccines in denaturing condition (FIG. 3A, left panel) are approximately 195 kDa. Upon reducing condition, the chimeric Ig-H and Ig-kappa components of the vaccines showed a molecular size of approximately 75 and 25 kDa, respectively (FIG. 3A, right panel). As reference, the molecular size of mouse IgM is also shown.

The chimeric vaccines were recognized by antibodies specific for the Ig constant domain, PyCSP B cell repeats, and costimulatory ligands, as revealed by western blot analysis (FIG. 3 B-D). Western blotting result of the chimeric vaccine molecules using anti-mouse IgG heavy chain was shown in FIG. 3B. The integrity of the chimeric Ig-H component of the vaccines was observed. FIG. 3C shows the western blotting result of chimeric vaccines using anti-PyCSP B cell repeats (NSLY) mAb. Only the PyBTh1 and PyBTh2 vaccine molecules, which express the PyCSP B cell repeats were recognized by the NSLY Ab. The PyTh1 and PyTh2 vaccine molecules that lack PyCSP B cell repeats were not recognized. This result shows the structural integrity of the PyCSP B cell repeats in the PyBTh1 and PyBTh2 vaccines. FIG. 3D shows the western blotting results of the chimeric vaccines using anti-mouse. IL-4 (upper panel) and anti-mouse B7.1 (CD80) (lower panel) mAbs. Both PyTh1 and PyBTh1 vaccine molecules that express mouse B7.1 costimulatory molecule were recognized by anti-B7.1 Abs. Both PyTh2 and PyBTh2 vaccine molecules that express mouse IL-4 costimulatory molecule were recognized by anti-IL-4 Abs. These results demonstrate the structural integrity of the costimulatory ligand of the vaccines.

Figure 4:
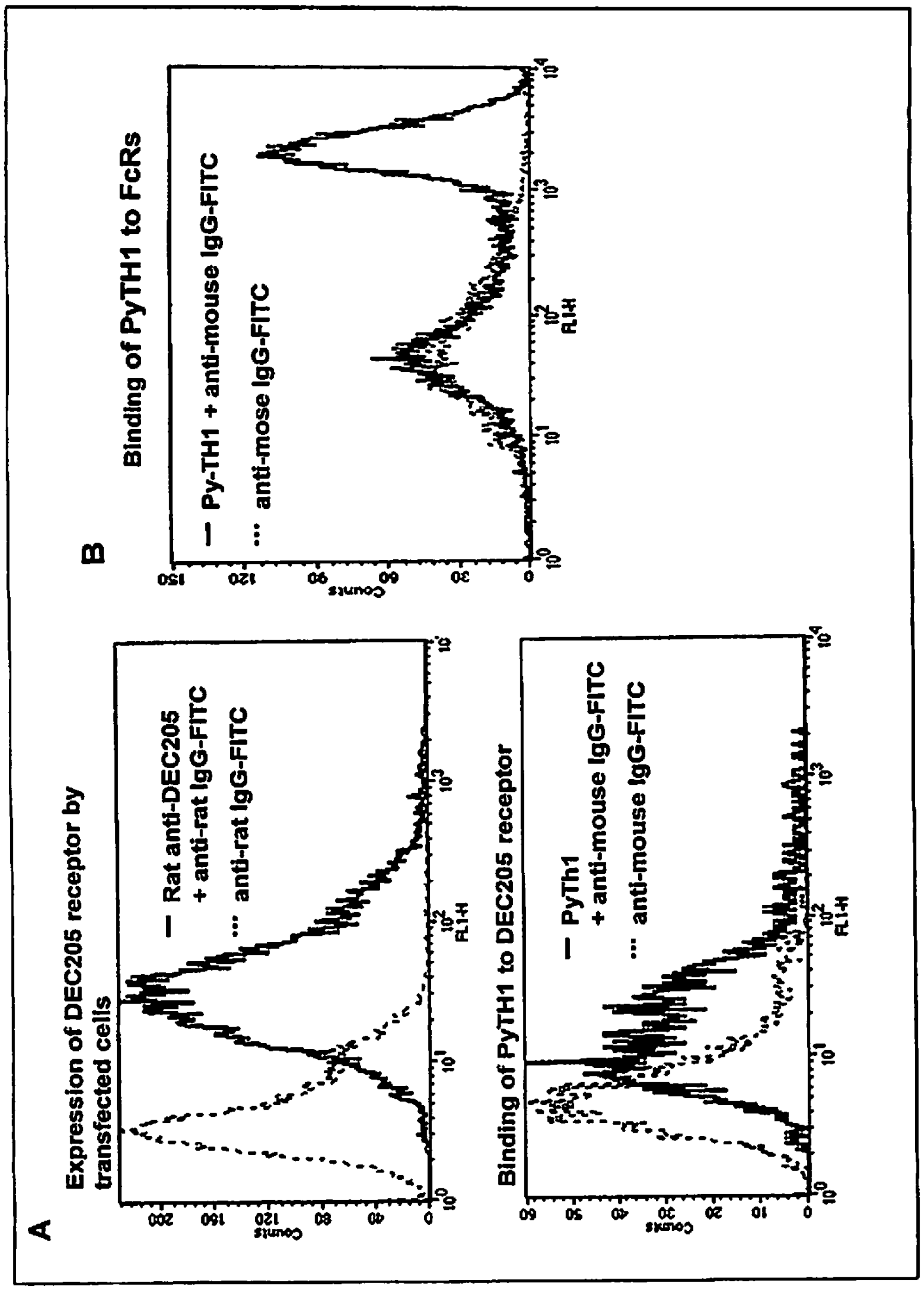
FIG. 4. Binding of chimeric molecules to DEC205 receptor and to FcRs. Panel A, the plasmid DNA encoding for DEC25 receptor was stably transfected into A204 cells. Upper histogram shows expression of DEC205 receptor on transfected cells as revealed by staining with rat anti-mouse DEC205. Binding of PyTh1 vaccine to DEC205 receptor is shown in the lower histogram. Panel B, binding of PyTh1 to FcRs.

Example 4: Ability of Chimeric Vaccines to Bind to DEC205 Receptor and to FcRs The Th1/Th2-polarizing vaccines are made of a mouse IgG2a scaffold with specificity for DEC205 receptor. The constant domain of mouse IgG2a is also able to bind with high-affinity to Fc receptors (FcRs). The results shown in FIG. 4, indicate the structural integrity of the Ig-H component of the vaccines and its ability to bind to FcRs expressed on APCs. The gene encoding for mouse DEC205 receptor (5.5 Kb) was amplified by RT-PCR from total RNA extracted from spleen cells of BALB/c mice and cloned into pcDNA3 vector expressing “Zeocin” resistance gene. The plasmid DNA encoding for DEC25 receptor was stably transfected into A204 cells. Upper histogram of FIG. 4A shows expression of DEC205 receptor on transfected cells as revealed by staining with rat anti-mouse DEC205. Binding of PyTh1 vaccine to DEC205 receptor is shown in the lower histogram.

Spleen cells from BALB/c mice were stimulated for 12 hour with 100 U/ml mouse IFNγ. Study has previously shown that IFNγ upregulates the expression of FcRs on monocytes/macrophages [13]. IFNγ-stimulated splenic cells were harvested and stained with the PyTh1 vaccine. Binding to FcRs was assessed by Fluorescence-activated cell sorting (FACS) (Becton Dickinson, Franklin Lakes, N.J.) in the FCS/SSC gated splenic monocyte cell population. The results were shown in FIG. 4B, which indicate the structural integrity of the Ig-H component of the vaccines and its ability to bind to FcRs expressed on APCs.

Example 5: Function of B7.1 and IL-4 Components of the Malaria Vaccine Reagents

Figure 5:
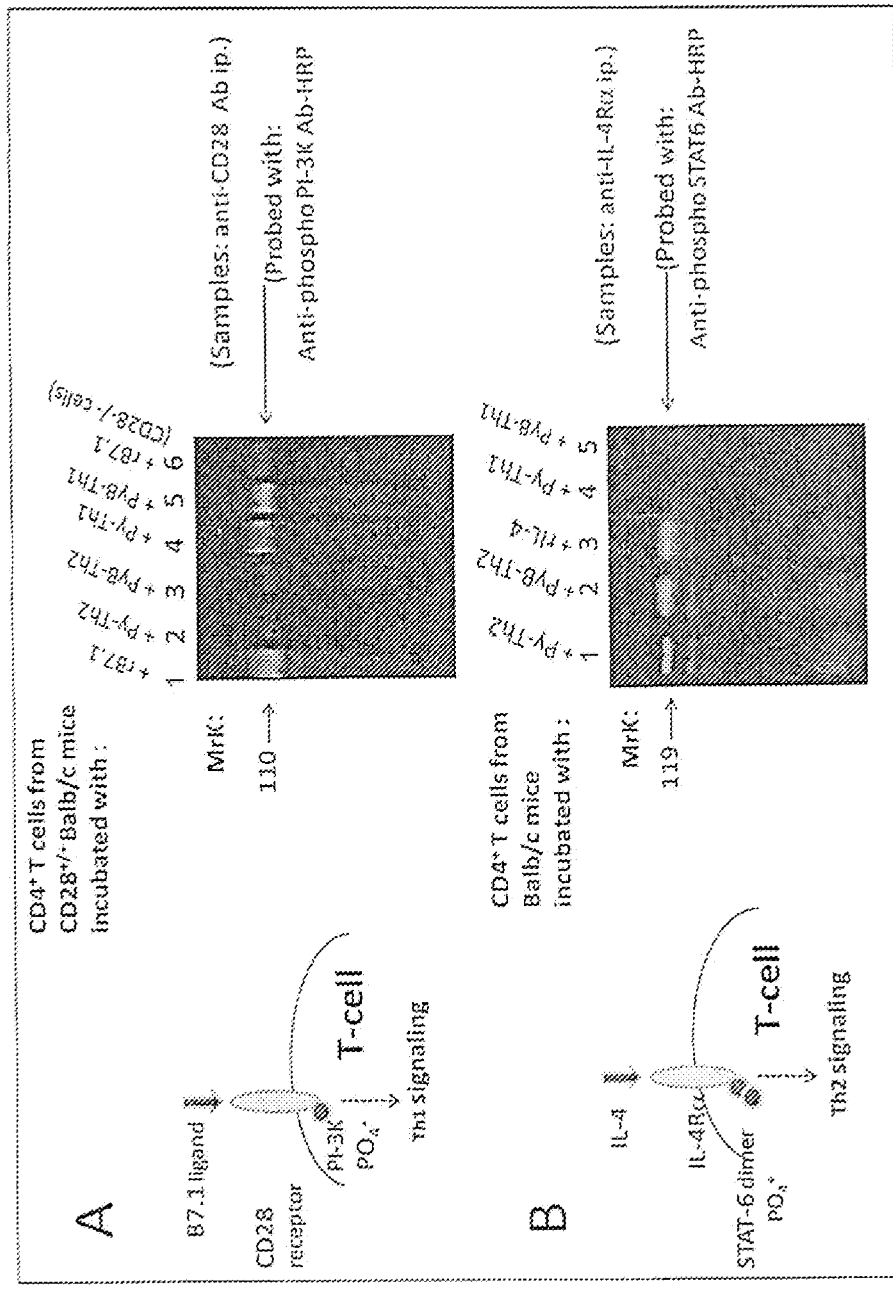
FIG. 5. Function of B7.1 and IL-4 components of the malaria vaccine reagents.

The costimulatory domains are also found to be fully functional as illustrated in FIG. 5. Negatively-sorted CD4 T-cells ($20\times10^6$ cells) from naïve CD28 or CD28 KO BALB/c mice were incubated for 10 minutes with the vaccines (5 μg), recombinant mouse B7.1 molecule (5 μg, positive control) generated in the lab, or recombinant mouse IL-4 (5 μg) in PBS at 37° C. Cells were washed in PBS, and lysed for 10 minutes in cold PBS containing 0.5% NP-40, a cocktail of protease inhibitors, and sodium vanadate. Cell lysates were immunoprecipitated for 2 hours at room temperature with CD28 mAb or IL-4Rα mAb (5 μg) followed by incubation for 10 minutes at room temperature with 50 μL of Agarose-Protein A conjugate and electrophoresis on 10% SDS-PAGE. Gels were electrotransferred on PVDF membranes, which were blocked in 5% milk and then probed overnight at 4° C. with phospho-PI-3K (p110) mAb-HRP or phosphor-STAT6 mAb-HRP conjugates. Membranes were washed 3 times and the HRP activity was developed in chemiluminiscence and recorded on a KODAK image system. FIG. 5A, left panel shows a schematic of the CD28-induced phosphorylation of PI-3K in T-cells, and the chemiluminiscence of CD28-induced phosphorylation of PI-3K p110 unit (MW=110 kDa) upon incubation of CD4 T-cells with rB7.1 molecule of the vaccine reagents was shown on the right. Phosphorylation of PI-3K p110 unit by rB7.1 molecules (positive control) was shown in lane 1 and phosphorylation of PI-3K p110 unit by Py-Th1 and PyB-Th1 reagents in CD28+ T-cells were shown in lanes 4 and 5. The lack of PI-3K p110 phosphorylation by the Py-Th2 and PyB-Th2 reagents and by rB7.1 in CD28 KO CD4 T-cells negative control were shown in lane 2 and 3 and lane 6, respectively. FIG. 5 B, left panel shows a schematic of the IL-4Rα-induced phosphorylation of STAT6 in T-cells. FIG. 5 B, right panel illustrates chemiluminiscence of IL-4Rα-induced phosphorylation of STAT6 (MW=119 kDa) upon incubation of $CD28^+$ CD4 T-cells with rIL-4 (positive control) or with the vaccine reagents. The phosphorylation of STAT6 by rIL-4 (positive control) was shown in lane 3. The phosphorylation of STAT6 by Py-Th2 and PyB-Th2 reagents were shown in lanes 1 and 2. The lack of STAT6 phosphorylation by the Py-Th1 and PyB-Th1 reagents were shown in lanes 4 and 5. In summary, these results demonstrate the chimeric vaccines preserve the structural integrity and biological functions.

Example 6: Immunogenicity of Th1/Th2 Vaccines a) Immunogenicity of the pyCSP B Cell Repeats Expressed by PyBTh1 and PyBTh2 Chimeric Vaccines.

Figure 6:
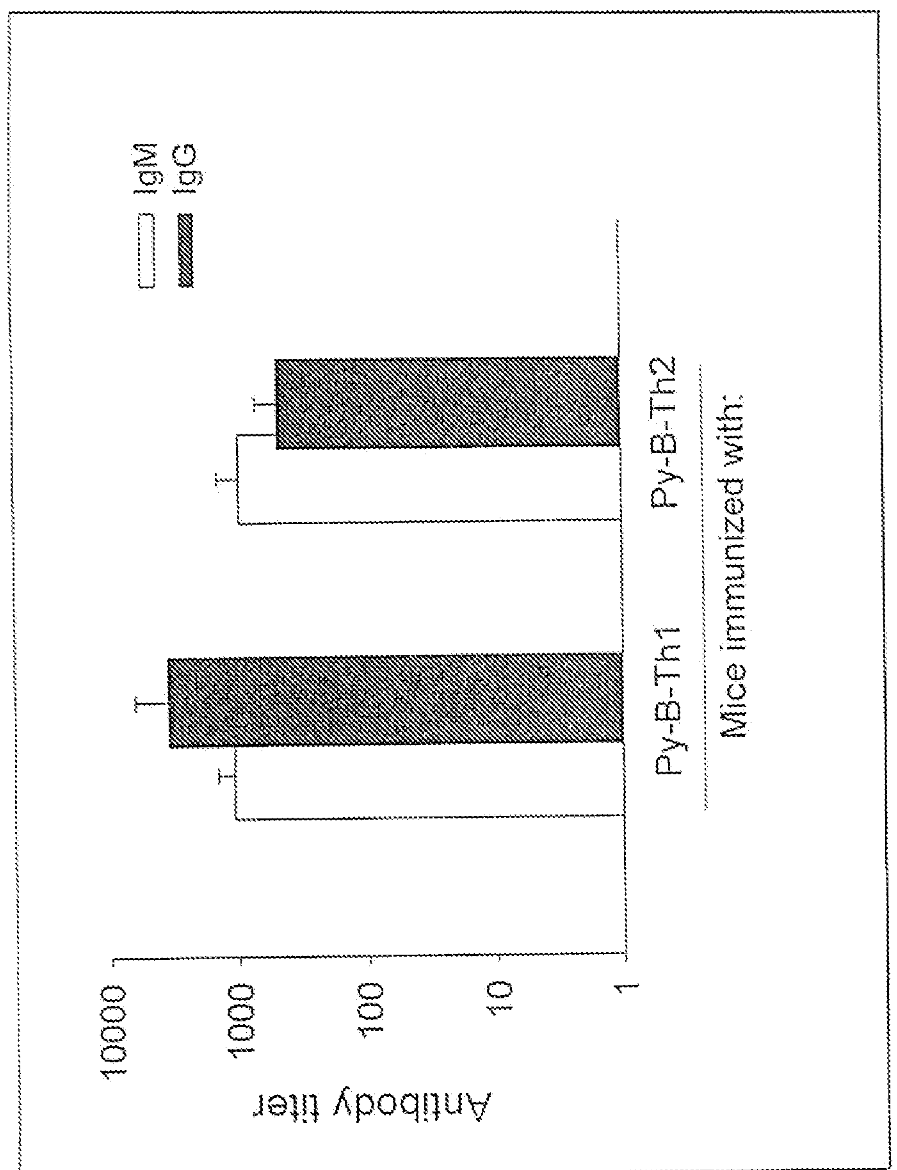
FIG. 6. Immunogenicity of the pyCSP B cell repeats expressed by PyBTh1 and PyBTh2 chimers.

C57BL/6 mice were injected intravenously with two doses of 100 micrograms of PyBTh1 or PyBTh2 chimeras administered two weeks apart. Mice were bled and sera was used to measure the titer of anti-CSP Abs by IFA using *Plasmodium yoelii* sporozoites dissected from salivary glands of infected Anopheles mosquitoes as described [14]. Data are expressed as mean±SD of three individual mice. The Py CSP B cell repeats expressed by the PyBTh1 and PyBTh2 chimeras are immunogenic, as revealed by their ability to elicit specific IgM and IgG antibodies upon immunization (FIG. 6).

b) Immunogenicity of the PyCSP CD4 T Cell Epitope Expressed by the Chimeric Vaccines.

BALB/c mice were injected intravenously with two doses of 100 micrograms of PyTh1 or PyTh2 chimeras administered two weeks apart. Non-immunized mice were used as control. Two weeks after the last immunization, mice were challenged intravenously with 50,000 infectious *P. yoelii* sporozoites and spleens were harvested 40 hours after the challenge. Splenic cells were stimulated in vitro for 3 days with 10 micrograms/ml of CSP peptide, 1 microgram/ml of Py-Th1 or Py-Th2 chimeras or left unstimulated. Data is expressed as cytokine concentration in cell culture supernatants as measured by Luminex (INVITROGEN®, San Diego, Calif.).

Figure 7A:
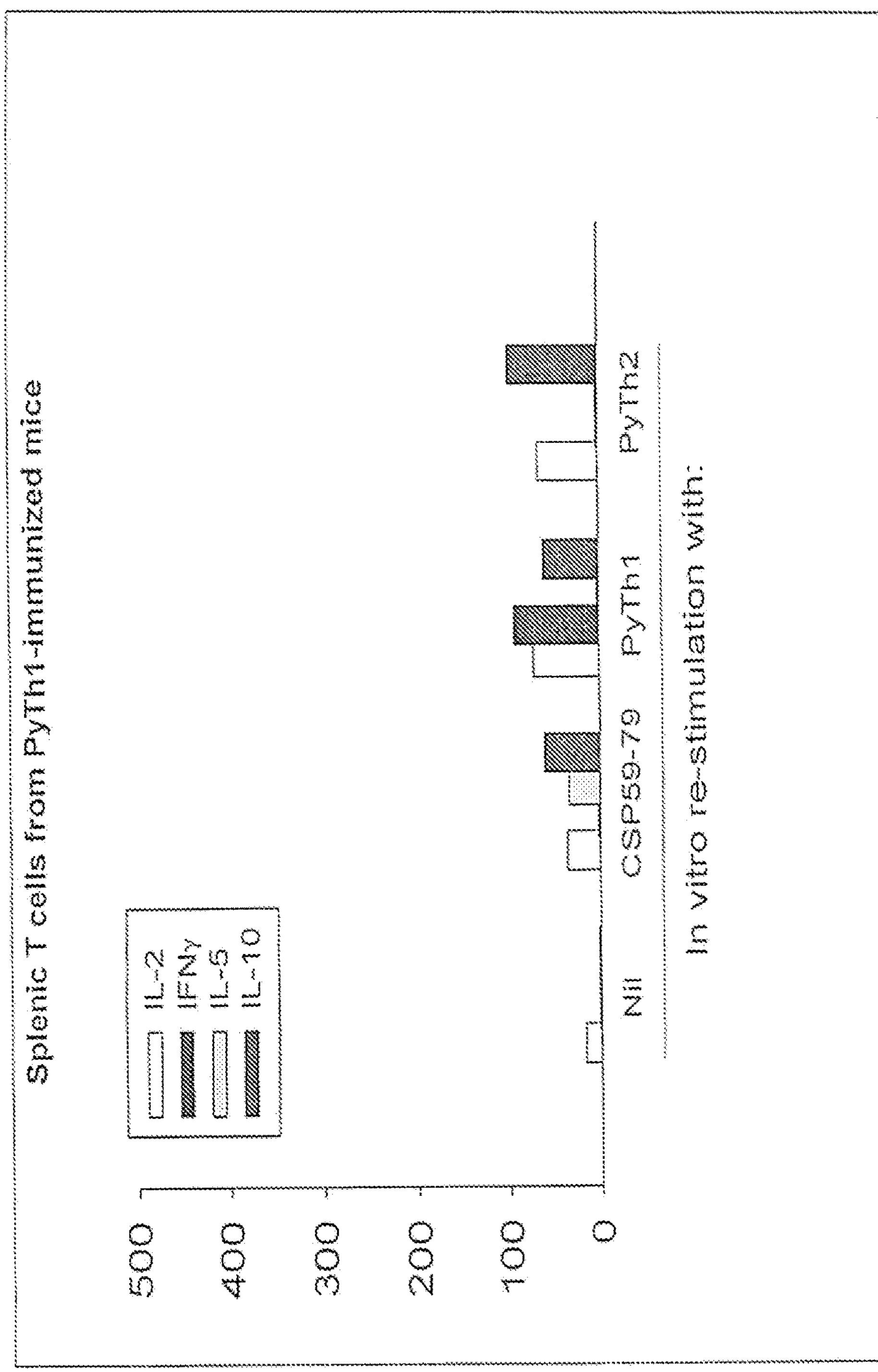
FIG. 7A. Immunogenicity of the PyCSP CD4 T cell epitope expressed by the chimera PyTh1.
Figure 7B:
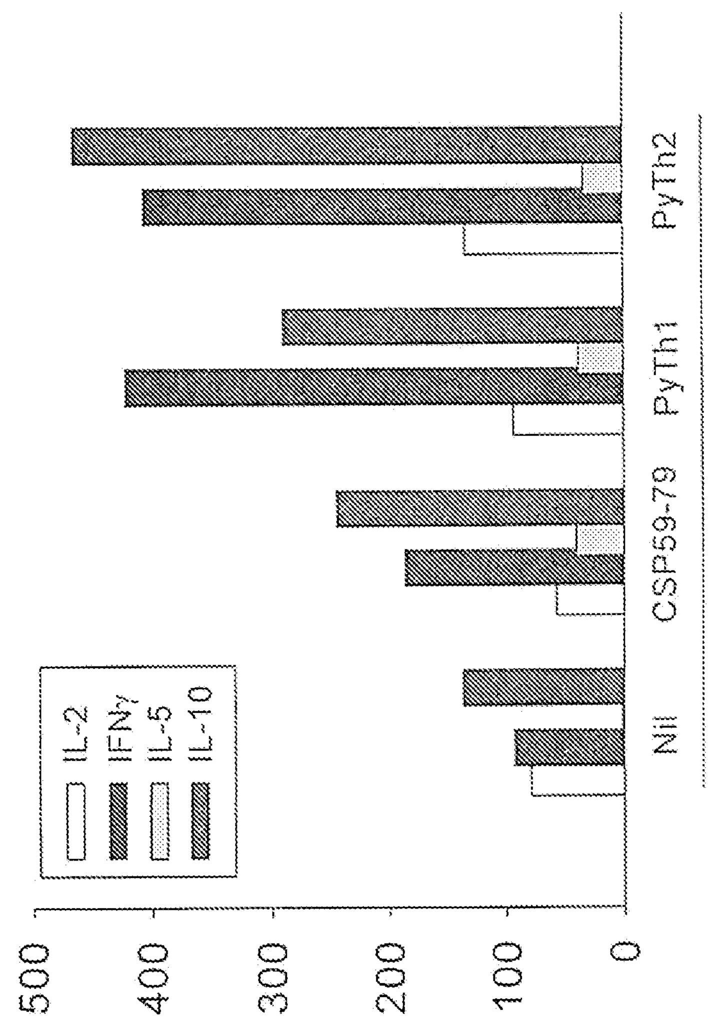
FIG. 7B Immunogenicity of the PyCSP CD4 T cell epitope expressed by the chimera PyTh 2.
Figure 7C:
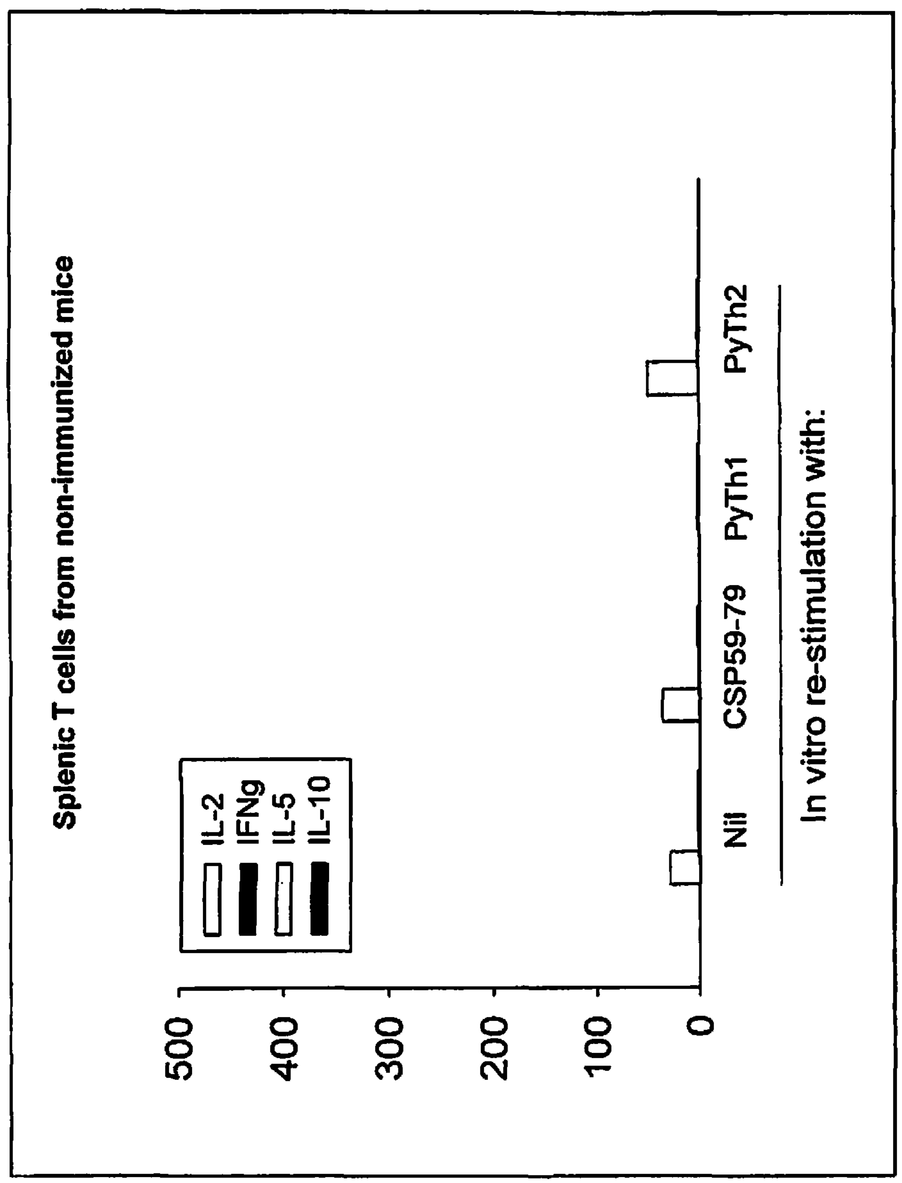
FIG. 7C Immunogenicity of the PyCSP CD4 T cell epitope expressed in non-immunized mice.

The PyCSP CD4 T cell epitope expressed by the chimeras is immunogenic as revealed by their ability to stimulate CSP-specific T cells upon immunization as shown in FIG. 7. To address the role of PyTh1 and PyTh2 chimeras to drive polarization of CSP-specific T cells towards a Th1 (inflammatory) or Th2 (anti-inflammatory) phenotype, splenic T cells from PyTh1 or PyTh2-immunized mice were re-stimulated in vitro with PyTh1 or PyTh2 chimeras. As illustrated in FIG. 7, upper panels, re-stimulation with PyTh1 chimeras resulted in increase production of IFN γ (inflammatory) cytokine, whereas re-stimulation with PyTh2 chimera enhanced production of IL-10 (anti-inflammatory) cytokine. In contrast, splenic T cells from naïve (non-immunized) mice stimulated with the PyTh1 or PyTh2 chimeras did not result in cytokine secretion (FIG. 7, lower panel), which demonstrates the specificity of chimeras in stimulating selectively CSP-specific T cells.

Example 7: Immunization with PyTh1 or PyTh2 Chimeras Significantly Reduces the Burden of Liver Stage Parasites Malaria sporozoites infect and replicate in liver (hepatocytes) cells. Infected hepatocytes release hundreds of liver-stage merozoites, which then move forward to infect erythrocytes. A massive infection of erythrocytes leads to the onset of malaria [7].

To investigate the efficacy of chimeric vaccines against liver stage parasites, BALB/c mice were injected intravenously with one or two doses (administered two weeks apart) of 100 micrograms of PyTh1 or PyTh2 chimeras. Non-immunized mice were used as control. Two weeks after the last immunization, mice were challenged intravenously with 50,000 infectious *P. yoelii* sporozoites and livers were harvested 40 hours after the challenge. Livers were used to isolate total RNA that was analyzed by real-time PCR using primers specific for the parasite 18S RNA. Data are expressed as the percentage of liver stage parasites in groups of three mice analyzed individually, relative to control (non-immunized) BALB/c mice.

Figure 8:
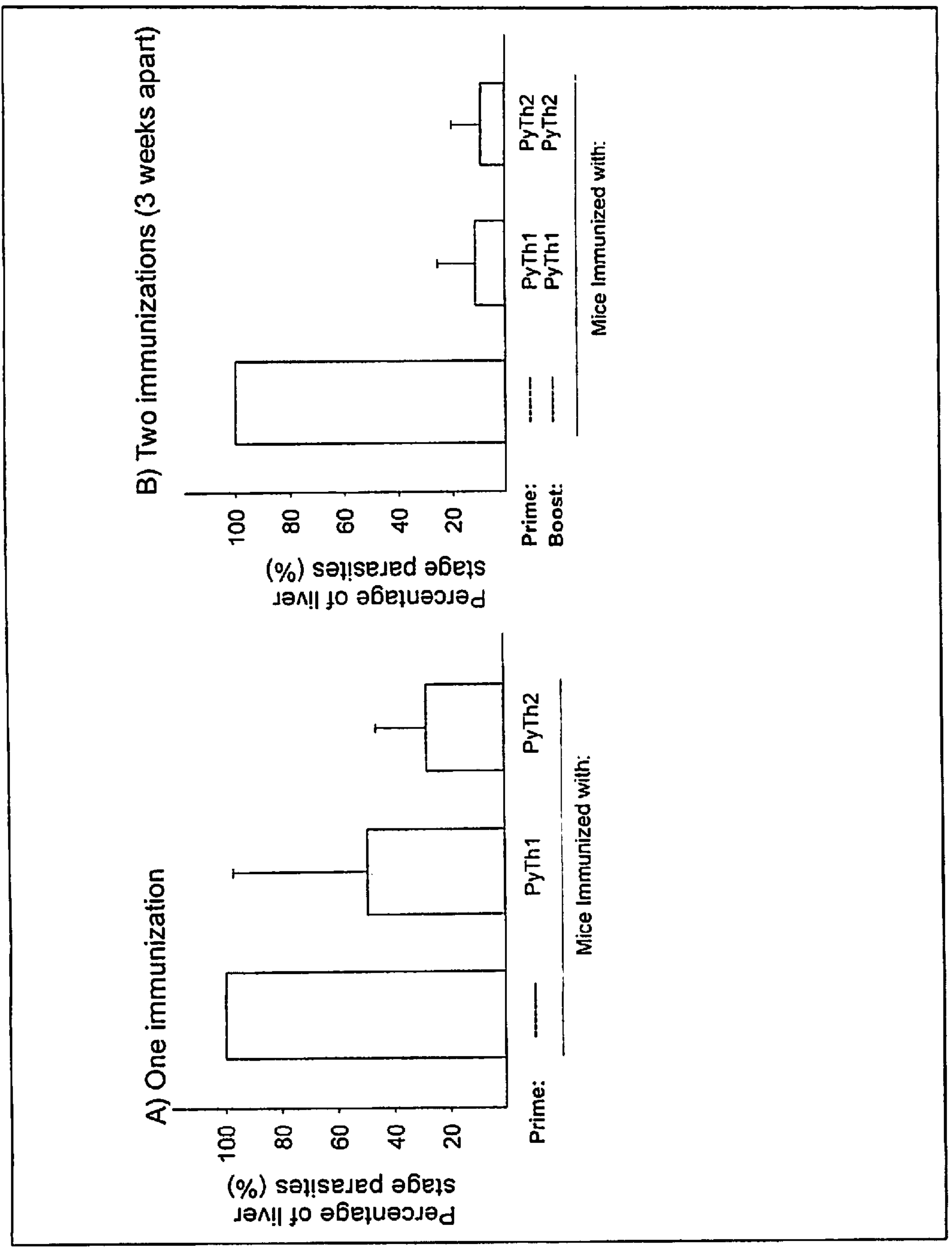
FIG. 8. Percentage of liver stage parasites after (A) One immunization, (b) two immunizations with the PyTh1 or PyTh2 chimeras.
Figure 9:
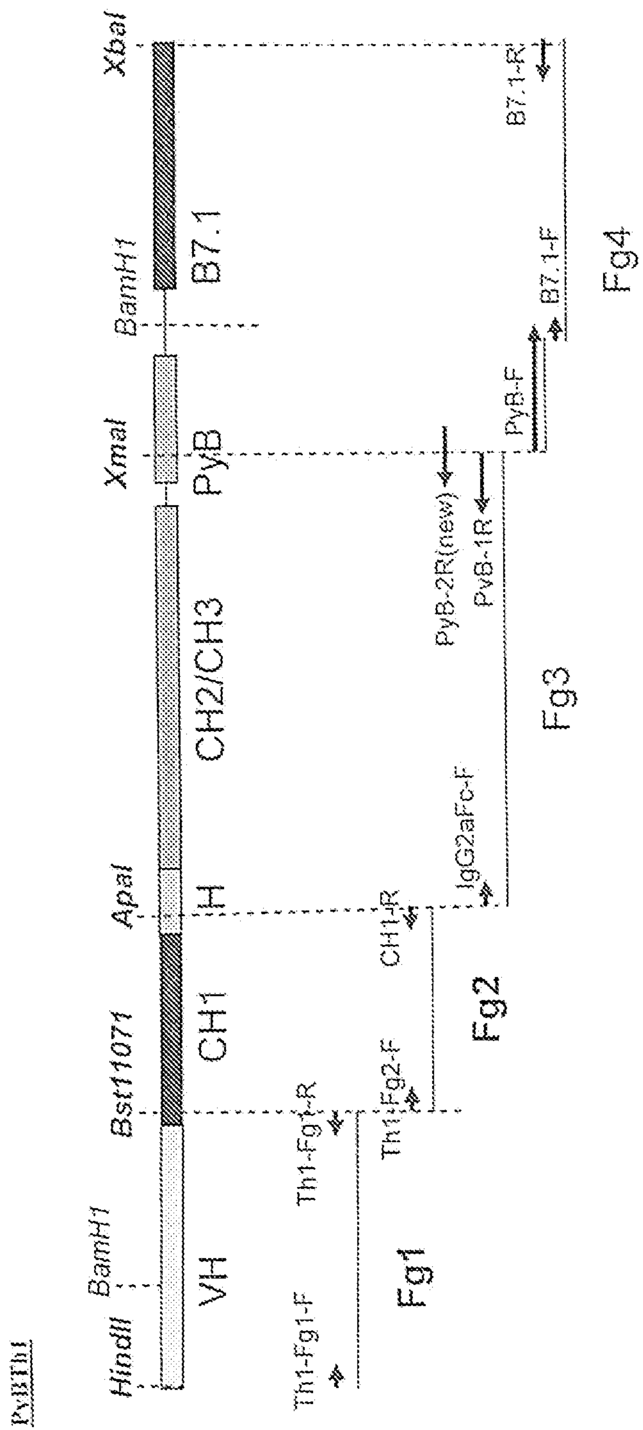
FIG. 9A Schematic representation of the primer sets used to encode chimeric molecules PyBTh1 heavy chain.
FIG. 9B Schematic representation of the primer sets used to encode chimeric molecules PyBTh2 heavy chain.
FIG. 9C Schematic representation of the primer sets used to encode chimeric molecules Kappa chain.
Figure 9B:
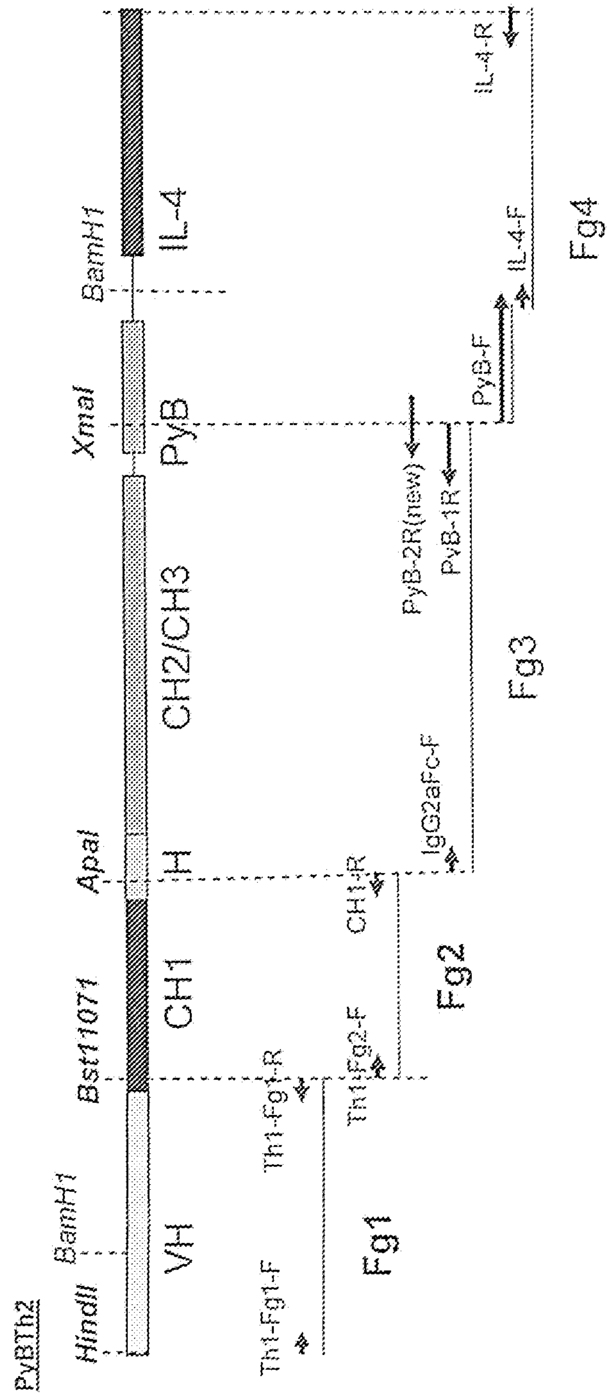
Figure 9C:
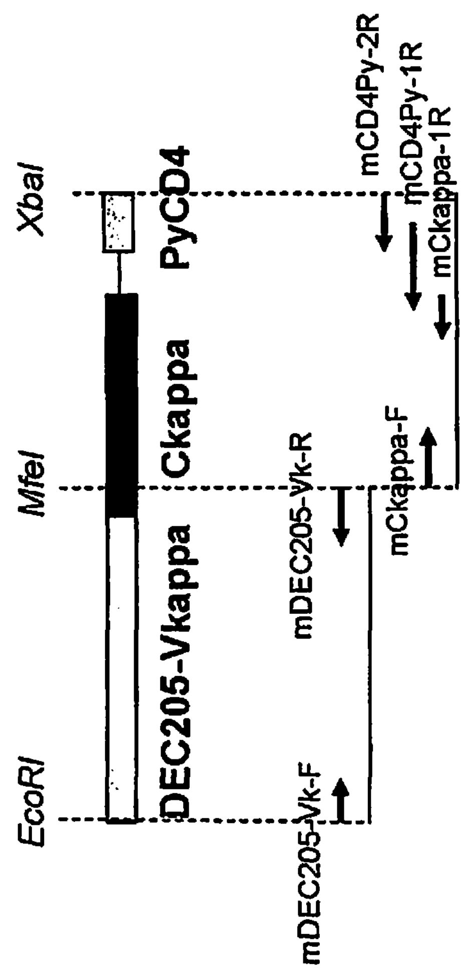
Figure 10:
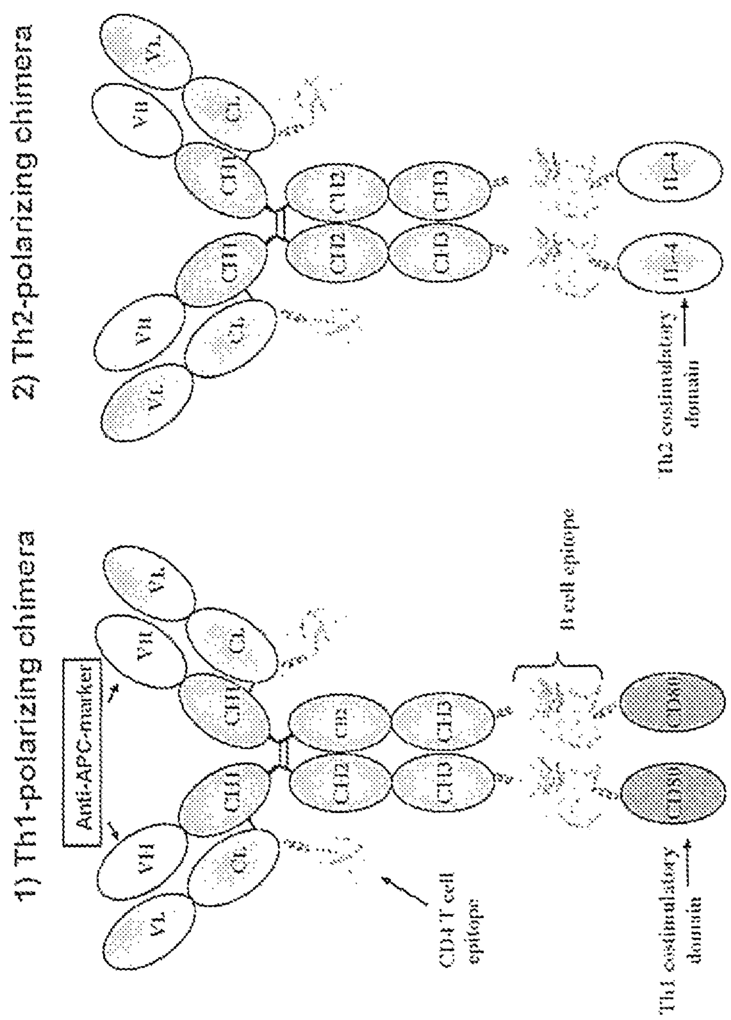
FIG. 10 Schematic representation of the chimeric molecules Th1 and Th2 polarizing chimera molecule.

As illustrated in FIG. 8, immunization with a single dose of the vaccines significantly reduced the amount of live stage parasites, and mice vaccinated twice with the PyTh1 or PyTh2 chimera were able to eliminate more than 90% of the infected hepatocytes.

Prophetic Example 8: Immunization with PyBTh1 or PyBTh2 Chimeras

Malaria sporozoites infect and replicate in liver (hepatocytes) cells. Infected hepatocytes release hundreds of liver-stage merozoites, which then move forward to infect erythrocytes. A massive infection of erythrocytes leads to the onset of malaria [7].

To investigate the efficacy of chimeric vaccines against liver stage parasites, BALB/c mice were injected intravenously with one or two doses (administered two weeks apart) of 100 micrograms of PyBTh1 or PybTh2 chimeras. Non-immunized mice were used as control. Two weeks after the last immunization, mice were challenged intravenously with 50,000 infectious *P. yoelii* sporozoites and livers were harvested 40 hours after the challenge. Livers were used to isolate total RNA that was analyzed by real-time PCR using primers specific for the parasite 18S RNA. Data are expressed as the percentage of liver stage parasites in groups of three mice analyzed individually, relative to control (non-immunized) BALB/c mice.

Prophetic Example 9: Immunization with Chimerias as Human Malaria Vaccine

To investigate the efficacy of chimeric vaccines against liver stage parasites in human, humanized mice (HLA-BR4) were injected intravenously with one or two doses (administered two weeks apart) of 100 micrograms of PyBTh1, PyTh1, PyBTh2 and PyTh2 chimeras. Non-immunized mice were used as control. Two weeks after the last immunization, mice were challenged intravenously with 50,000 infectious *P. yoelii* sporozoites and livers were harvested 40 hours after the challenge. Livers were used to isolate total RNA that was analyzed by real-time PCR using primers specific for the parasite 18S RNA. Data are expressed as the percentage of liver stage parasites in groups of three mice analyzed individually, relative to control (non-immunized) BALB/c mice.

REFERENCES

1. Adorini et al. Competition for antigen presentation in living cells involves exchange of peptides bound by class II WIC molecules. Nature 342: 800-803 (1989).
2. Arndt et al. Functional HLA-DM on the surface of B cells and immature dendritic cells. EMBO J. 19:1241-1251 (2000).
3. Bona, C. A., Casares, S. & Brumeanu, T-D. Towards the development of T cell vaccines. *Immunol. Today* 19:126-132 (1998).
4. Brumeanu, T., Casares, S., Harris, P., Dehazya, P., Wolf, I., von Boehmer, H. & Bona, C., Immunopotency of a viral peptide assembled on the carbohydrate moieties of self immunoglobulins. *Nature Biotechnology* 14: 722-725 (1996).
5. Brumeanu, T-D., Casares. S., Bot, A., Bot, S. & Bona, C. A. Immunogenicity of a contiguous T-B viral epitope from hemagglutinin of A/PR/8/34 influenza virus. *J. Virol.* 71: 5473-5480 (1997).
6. Casares, S., Bona, C. A. & Brumeanu, T-D. Engineering and characterization of a murine MHC-immunoglobulin chimera expressing an immunodominant CD4 T viral epitope. *Protein Engineering* 10:1295-1301 (1997).
7. Casares S, Richie T L. 2009. Immune evasion by malaria parasites: a challenge for vaccine development. *Curr Opin Immunol.* 21:321-30.
8. Casares, S., Bona, C. A. & Brumeanu, T. D. Enzymatically mediated engineering of multivalent MHC class II-peptide chimeras. *Protein Engineering* 14: 195-200 (2001).
9. Casares, S., Stan, A. C., Bona, C. A. & Brumeanu, T-D. Antigen-specific downregulation of T cells by doxorubicin delivered through a recombinant MHC II-peptide chimera. *Nature Biotechnology* 19:142-147 (2001).
10. Casares, S. Bona, C. A. & Brumeanu, T. D. Immunoregulation of antigen-specific T cells by MHC-peptide chimeras. *Int. Rev. Immunol.* 20:547-574 (2001).
11. Dolfi, D V & Katsikis, P D. CD28 and CD27 costimulation of CD8+ T cells: a story of survival. *Adv Exp Med Biol.* 590:149-70 (2007).
12. Loo, Y M. & Gale, M. Viral regulation and evasion of the host response. *Curr Top Microbiol Immunol.* 316:295-313 (2007).
13. Preda I, McEvoy R C, Lin M, Bona C A, Rapaport R, Brumeanu T D, Casares S. 2005. Soluble, dimeric HLA DR4-peptide chimeras: an approach for detection and immunoregulation of human type-1 diabetes. Eur. J. Immunol. 135:2762, 2005).
14. Sedegah M, Rogers W O, Belmonte A, Belmonte M, Banania G, Patterson N, Ferrari M, Kaslow D C, Carucci D J, Richie T L, Doolan D L. 2006. Vaxfectin enhances immunogenicity and protective efficacy of *P. yoelii* circumsporozoite DNA vaccines. Vaccine 24:1921-7.
15. Rudd C E, Taylor A, Schneider H. 2009. CD28 and CTLA-4 coreceptor expression and signal transduction. Immunol. Rev. 229:12-26.
16. Takeda K, Kishimoto T, Akira S. 1997. STAT6: its role in interleukin 4-mediated biological functions. J. Mol Med. 75:317-26.

The invention claimed is:

1. A malaria vaccine comprises a chimeric molecule, wherein said chimeric molecule comprising:

a) an immunoglobulin scaffold, wherein said immunoglobulin scaffold comprising a domain specific for binding to a protein on an antigen presenting cell;

b) a costimulatory domain linked to a heavy chain of said immunoglobulin scaffold; and c) a circumsporrozoite protein-specific (CSP-specific) T cell epitope linked to a c-terminus of a light chain of said immunoglobulin scaffold.

2. The malaria vaccine of claim 1, wherein said chimeric molecule further comprising at least one malaria-specific B cell epitope linked to the C-terminus of said heavy chain of said immunoglobulin scaffold.

3. The malaria vaccine of claim 1, wherein said immunoglobulin scaffold is a humanized immunoglobulin.

4. The malaria vaccine of claim 1, wherein said immunoglobulin scaffold comprising at least one domain of an immunoglobulin Ig.G.

5. The malaria vaccine of claim 4, wherein said immunoglobulin is IgG1, IgG2, IgG3, or IgG4.

6. The malaria vaccine of claim 1, wherein said antigen presenting cell is selected from the group consisting of dendritic cells, Langerhans cells, B cells, monocytes, macrophages, endothelial cells, and granulocytes.

7. The malaria vaccine of claim 1, wherein said antigen presenting cell is a dendritic cell.

8. The malaria vaccine of claim 7, wherein said protein on said antigen presenting cell is CD205.

9. The malaria vaccine of claim 1, wherein said costimulatory domain is linked to C-terminus of said heavy chain of said immunoglobulin.

10. The malaria vaccine of claim 1, wherein said costimulatory domain is selected from the group consisting of B7.1 (CD80), B7.2 (CD86), interleukin 2, and Interleukin 12.

11. The malaria vaccine of claim 1, wherein said costimulatory domain is B7.1.

12. The malaria vaccine of claim 1, wherein said costimulatory domain is selected from the group consisting of interleukin-4, interleukin-5, interleukin-6, interleukin-10, interleukin-13.

13. The malaria vaccine of claim 1, wherein said costimulatory domain comprising interleukin-4.

14. The malaria vaccine of claim 1, wherein said T cell epitope is a CD4 T cell epitope or a CD8 T cell epitope.

15. The malaria vaccine of claim 2, wherein said malaria-specific B cell epitope comprising at least one immunogenic polypeptide selected from antigens consisting of circumsporrozoite protein (CSP), thrombospondin related adhesive protein/sporozoites surface protein-2 (TRAP/SSP2), liver stage antigen-1 (LSA1), merozoite surface protein-1 (MSP1), apical membrane antigen-1 (AMA-1).

16. The malaria vaccine of claim 15, wherein said malaria-specific B cell epitope is linked to said C-terminus of said heavy chain of said immunoglobulin scaffold by a glycine linker.

17. The malaria vaccine of claim 16, wherein said costimulatory domain is linked to said malaria-specific B cell epitope.

18. An immunogenic composition, comprising the malaria vaccine of claim 1.

19. The malaria vaccine of claim 17, wherein said costimulatory domain is linked to said pathogen-specific B cell epitope by a glycine linker.

* * * * *